(12) United States Patent
Phillips et al.

(10) Patent No.: US 8,462,347 B2
(45) Date of Patent: Jun. 11, 2013

(54) METHOD AND APPARATUS FOR SILOXANE MEASUREMENTS IN A BIOGAS

(75) Inventors: Charles Mark Phillips, Sicklerville, NJ (US); Barbara Marshik-Geurts, Methuen, MA (US); Leonard I. Kamlet, Andover, MA (US); Martin L. Spartz, Ellington, CT (US); Vidi Saptari, Cambridge, MA (US)

(73) Assignee: MKS Instruments, Inc., Andover, MA (US)

( * ) Notice: Subject to any disclaimer, the term of this patent is extended or adjusted under 35 U.S.C. 154(b) by 500 days.

(21) Appl. No.: 12/720,542

(22) Filed: Mar. 9, 2010

(65) Prior Publication Data

US 2010/0223015 A1    Sep. 2, 2010

Related U.S. Application Data

(63) Continuation-in-part of application No. 12/567,981, filed on Sep. 28, 2009, now abandoned, which is a continuation of application No. 12/119,244, filed on May 12, 2008, now Pat. No. 7,595,887, which is a continuation of application No. 11/240,799, filed on Sep. 30, 2005, now Pat. No. 7,372,573.

(51) Int. Cl.
*G01B 9/02*    (2006.01)
*G01J 3/45*    (2006.01)
*G01N 21/00*    (2006.01)

(52) U.S. Cl.
USPC .......................................... 356/451; 356/437

(58) Field of Classification Search
USPC .................. 356/432, 436, 437, 451
See application file for complete search history.

(56) References Cited

U.S. PATENT DOCUMENTS

| 4,183,670 A | 1/1980 | Russell |
| 4,538,910 A | 9/1985 | Doyle |
| 5,200,543 A | 4/1993 | Inomata et al. |
| 5,341,207 A | 8/1994 | Tank et al. |
| 5,440,143 A * | 8/1995 | Carangelo et al. ............ 250/573 |
| 5,457,316 A * | 10/1995 | Cohen et al. ................. 250/286 |
| 5,541,728 A | 7/1996 | Dierking |

(Continued)

FOREIGN PATENT DOCUMENTS

| JP | 2006098387 A * | 4/2006 |
| WO | WO 98/27416 | 6/1998 |
| WO | WO 00/07411 | 2/2000 |

OTHER PUBLICATIONS

Schweigkofler, Martin et al. "Removal of siloxanes in biogases". Journal of Hazardous Materials, vol. B83, 2001, pp. 183-196.*

(Continued)

*Primary Examiner* — Michael A Lyons
(74) *Attorney, Agent, or Firm* — Prokauer Rose LLP

(57) ABSTRACT

A method for monitoring of siloxane compounds in a biogas includes the step of generating a first absorption spectrum based on a ratio of a first spectral measurement and a second spectral measurement. The first spectral measurement is from a non-absorptive gas having substantially no infrared absorptions in a specified wavelength range of interest and the second spectral measurement is from a sample gas comprising the biogas. The method also includes the step of calculating a concentration of at least one siloxane compound in the biogas using a second absorption spectrum based on, at least, a first individual absorption spectrum for a known concentration of the at least one siloxane compound.

30 Claims, 11 Drawing Sheets

U.S. PATENT DOCUMENTS

| | | | |
|---|---|---|---|
| 5,777,735 | A | 7/1998 | Reagen |
| 6,784,428 | B2 | 8/2004 | Rabolt et al. |
| 7,372,573 | B2 | 5/2008 | Spartz et al. |
| 7,595,887 | B2 | 9/2009 | Spartz et al. |
| 7,956,761 | B2 * | 6/2011 | Polak et al. ............ 340/632 |
| 2003/0184733 | A1 | 10/2003 | Kameoka |
| 2006/0066824 | A1 | 3/2006 | Knappe et al. |
| 2007/0182965 | A1 * | 8/2007 | Kamlet et al. ............ 356/437 |
| 2010/0079764 | A1 | 4/2010 | Spartz et al. |

OTHER PUBLICATIONS

Heise, H.M., et al. "Calibration Method for the Infrared-Spectrometirc Trace Gas Analysis," *Fresenius' Journal of Analytical Chemistry*, 332(4):pp. 387-400 (Jan. 1985).

MKS Gas Analysis, "MultiGas Purity," 4 pages (Jun. 2004).

MKS Gas Analysis, "MultiGas 2030," 4 pages (Nov. 2004).

MKS Gas Analysis, "MultiGas 2030 HS," 4 pages (Aug. 2005).

MKS Gas Analysis, "Process Insight," 6 pages (Aug. 2005).

Ragunathan, N. et al., "Gas Chromatography with Spectroscopic Detectors," *Journal of Chromatography A.*, 856:pp. 349-397 (1999).

Smiths brochure #1, "Smiths Detection GasID Portable Gas & Vapor Identifier," 2 pages (2004).

Smiths brochure #2, "Smiths Detection GasID Portable Gas & Vapor Identifier," 2 pages (2005).

The International Search Report for International Application No. PCT/US2006/038550, Date of Mailing Jul. 3, 2008 (6 pages).

Gasmet, "Multicomponent On-line FTIR Gas Analysis," 11 pages (available prior to Sep. 30, 2005).

Gasmet, "Gasmet Dx-4000 Multicomponent FTIR Gas Analyzer," 2 pages (available prior to Sep. 30, 2005).

Gasmet, " Gasmet Dx-4015 Multicomponent FTIR Gas Analyzer," 2 pages (available prior to Sep. 30, 2005).

Thermo Electron Corporation Product Overview, "MIRAN SapphIRe Portable Infrared Ambient Analyzer," 4 pages (available prior to Sep. 30, 2005).

Dewil et al., "Energy Use of Biogas Hampered by the Presence of Siloxanes," Elseview, Energy Conversion & Management, 47 (2006), pp. 1711-1277.

Ignatyev et al., "Vibrational Spectra of Trimethylsilanol the Problem of the Assignment of the Sioh Group Frequencies," Elsevier, Spectrochimica Acta Part A 60 (2004) pp. 1169-1178.

The International Search Report for International Application No. PCT/US2013/021899, Date of Mailing Apr. 16, 2013 (12 pages).

* cited by examiner

METHOD AND APPARATUS FOR SILOXANE MEASUREMENTS IN A BIOGAS

CROSS-REFERENCE TO RELATED APPLICATIONS

The present application is a continuation-in-part of prior co-pending U.S. application Ser. No. 12/567,981 filed on Sep. 28, 2009, which is a continuation of prior U.S. application Ser. No. 12/119,244 filed on May 12, 2008, which is a continuation of prior U.S. application Ser. No. 11/240,799, filed on Sep. 30, 2005, the entire disclosures of which are incorporated by reference herein.

FIELD OF THE INVENTION

The invention generally relates to absorption spectrometers, and more particularly to detecting trace amounts of chemical warfare agents, toxic industrial chemicals, and other trace compounds that can be found in ambient air. The invention also relates to monitoring and measuring concentrations of siloxane compounds in, for example, a biofuel or biogas.

BACKGROUND OF THE INVENTION

Spectroscopy is the study of the interaction between electromagnetic radiation and a sample (e.g., containing one or more of a gas, solid and liquid). The manner in which the radiation interacts with a particular sample depends upon the properties (e.g., molecular composition) of the sample. Generally, as the radiation passes through the sample, specific wavelengths of the radiation are absorbed by molecules within the sample. The specific wavelengths of radiation that are absorbed are unique to each of the molecules within the specific sample. By identifying which wavelengths of radiation are absorbed, it is therefore possible to identify the specific molecules present in the sample.

Infrared spectroscopy is a particular field of spectroscopy in which, for example, the types of molecules and the concentration of individual molecules within a sample are determined by subjecting the sample (e.g., gas, solid, liquid or combination thereof) to infrared electromagnetic energy. Generally, infrared energy is characterized as electromagnetic energy having wavelengths of energy between about 0.7 µm (frequency 14,000 $cm^{-1}$) and about 1000 µm (frequency 10 $cm^{-1}$). Infrared energy is directed through the sample and the energy interacts with the molecules within the sample. The energy that passes through the sample is detected by a detector (e.g., an electromagnetic detector). The detected signal is then used to determine, for example, the molecular composition of the sample and the concentration of specific molecules within the sample.

One particular type of infrared spectrometer is the Fourier Transform Infrared (FTIR) spectrometer. They are used in a variety of industries, for example, air quality monitoring, explosive and biological agent detection, semiconductor processing, and chemical production. Different applications for FTIR spectrometers require different detection sensitivity to enable a user to distinguish between which molecules are present in a sample and to determine the concentration of the different molecules. In some applications, it is necessary to identify the concentration of individual molecules in a sample to within about one part per billion (ppb). As industrial applications require increasingly better sensitivity, optimization of existing spectroscopy systems and utilization of new spectroscopy components can enable the system to repeatably and reliably resolve smaller and smaller concentrations of molecules in samples.

FTIR spectrometers can also be used to monitor concentrations of compounds, e.g., in gases. Biofuels (e.g., biogas) are used to power various equipment, including turbine generators. The biogas is burned to power the equipment. Biogas (e.g., gas from animal waste, wastewater or a landfill) can include, a variety of compounds, including, siloxane compounds. Siloxane compounds in the biogas are also burned which creates oxides (e.g., $SiO_2$ (e.g., silica, or sand)). The $SiO_2$ can coat both the turbine blades as well as the turbine bearings, resulting in decreased performance or even failure of the turbine. The coating process is accelerated with higher levels of siloxane in the biogas. Biogas producers usually use an activated charcoal filter to trap the siloxanes, however, when the filter is expended the siloxane level rises.

Traditional methods for monitoring concentrations of siloxane compounds in a biogas are performed offline by analyzing samples taken from the biogas. For example, traditional techniques involve using GC/MS (i.e., gas chromatography/mass spectrometry) techniques to separate the siloxanes from the background gas and measure them. To analyze the sample gas, a sample is grabbed for analysis and run on the GC/MS system. A field sample is usually taken from the gas stream and introduced into either a stainless steel canister, a Tedlar sample bag or collected using a Methanol solvent impinger. This sample is then transported back to the analytical lab and analyzed; the analytical result is usually not known for days. Samples have the tendency to let components condense out which makes it hard to assess the true composition in the sample. Samples taken in this manner also only provide a single shot in time at which the contents are analyzed and therefore, may not be representative of the true composition of the sample. The GC/MS analysis of the sample can also take several hours to analyze the siloxane compounds in the sample which may be too late to allow for operator intervention. If a rise in siloxane levels had occurred, the opportunity to perform any actionable recourse may have already passed. Enhancing the ability to monitor and measure concentrations of siloxane in a biogas can enable greater turbine life. Furthermore, being able to monitor and quickly detect and quantify siloxane compounds can provide greater time for actionable recourse/intervention.

SUMMARY OF THE INVENTION

Spectroscopy can be used to detect, identify, and/or quantify trace amounts of siloxane compounds in, for example, a biogas (e.g., identify the concentration of individual siloxane compounds in a sample biogas to within about five parts per billion (ppb)). Trace amounts of both cyclic siloxanes (e.g., D3-siloxane, D4-siloxane, D5-siloxane and D6-siloxane) and linear siloxanes (L2-siloxane, L3-siloxane, L4-siloxane and L5-siloxane) in a biogas can be detected and quantified. Concentrations of siloxane can be measured in-situ (e.g., at the site of, for example, a landfill, animal waste site or wastewater site) and in real time (e.g., processing and analyzing the content of the sample biogas at a site without having to obtain a sample and analyze the sample at a laboratory at a relatively later point in time). An in-line continuous monitor can sense a rise in siloxane levels in real time and notify the operator or automatically shut down the process, preventing unnecessarily exposing the turbines to $SiO_2$.

A sample that includes agents (e.g., compounds) having substantially higher infrared absorptions (e.g., interfering absorbers), as compared to other agents in the sample can present problems in FTIR spectroscopy because FTIR relies on subjecting a sample to infrared energy. Interfering absorbers in the sample prevent effective detection and measurement of concentrations of the other agents to be detected in the sample which have substantially lower infrared absorptions. A biogas can include molecules such as, for example, siloxane compounds, hydrocarbon compounds (e.g., methane or ethane), water, or carbon dioxide. The hydrocarbon compounds in the biogas can have relatively high infrared absorptions at certain wavelengths (e.g., absorption of about 0.055 at a wavelength of about 7.8 microns for ethane) as compared to siloxane compounds (e.g., an absorption of about 0.001 at a wavelength of about 7.8 microns for a D4 siloxane). The hydrocarbons can therefore be interfering absorbers. Siloxane compounds can have relatively higher infrared absorptions in a wavelength range of about 8 microns to about 12 microns (e.g., an absorption of about 0.075 at about 8.2 microns and 0.125 at about 11 microns for D4 siloxane). Therefore, concentrations of siloxane compounds in a sample biogas can be measured by taking spectral measurements in a wavelength range of interest (e.g., about 8 microns to about 12 microns), even in the presence of hydrocarbon compounds or other interfering absorbers. The wavelength range of interest can be selected where the major components of the biogas (e.g., $H_2O$, $CO_2$, $CH_4$) do not have large absorbances. The siloxane compounds may have overlapping absorbances with other hydrocarbons in the wavelength range of interest. Multivariate analysis methods can be used to distinguish the contributions between the siloxane compounds and the other hydrocarbons, as well as to assess the contributions that are due strictly to the siloxane compounds.

In one aspect, the invention features a method for monitoring of siloxane compounds in a biogas. The method includes the step of generating a first absorption spectrum based on a ratio of a first spectral measurement from a non-absorptive gas having substantially no infrared absorptions in a specified wavelength range of interest and a second spectral measurement from a sample gas comprising the biogas. The method also includes calculating a concentration of at least one siloxane compound in the biogas using a second absorption spectrum. The second absorption spectrum is based on, at least, a first individual absorption spectrum for a known concentration of the at least one siloxane compound.

In one embodiment, a processor is used to calculate a concentration of at least one siloxane compound in the biogas using a chemometric algorithm. For example, a processor can be used to perform multiple regression analysis using the first absorption spectrum and the second absorption spectrum to calculate the concentration of at least one siloxane compound in the biogas. Multiple regression analysis can be performed using Classical Least Squares (CLS), Partial Least Squares (PLS), Inverse Least Squares (ILS) or Principal Component Analysis (PCA).

The second absorption spectrum can be created based on, at least, the first individual absorption spectrum and individual absorption spectra for one or more additional siloxane compounds, hydrocarbon compounds, water or carbon dioxide. The second absorption spectrum can be a model based on known concentrations of the siloxane compounds, hydrocarbon compounds, water or carbon dioxide. In some embodiments, the second absorption spectrum is a model based on, at least, the first individual absorption spectrum. A concentration of at least one siloxane compound can be calculated by providing at least one variable representing the concentration of the at least one siloxane compound and determining a value for the at least one variable such that that the second absorption spectrum is substantially similar to the first absorption spectrum (e.g., mathematically fitting the second absorption spectrum to the first absorption spectrum).

In some embodiments, the concentration of at least one siloxane compound is calculated using a processor, in real-time (e.g., results of quantifying concentrations of siloxane compounds obtained in seconds or minutes) and in-situ (e.g., in-line or in a device in fluid communication with a source of the biogas and without the need for grabbing a sample). The second spectral measurement can be taken over an acquisition period of about 10 seconds to about 20 seconds.

In some embodiments, the at least one siloxane compound is selected from a group consisting of L2-siloxane, L3-siloxane, L4-siloxane, L5-siloxane, D3-siloxane, D4-siloxane, D5-siloxane, or D6-Siloxane.

The non-absorptive gas and the biogas can be provided to a sample cell. In some embodiments, the sample cell includes a concave reflective field surface at a first end of the sample cell and a substantially spherical, concave reflective objective surface at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface.

In another aspect, the invention features a method for monitoring a level of at least one siloxane compound in a biogas. The method includes the step of providing a non-absorptive gas to a sample cell, the non-absorptive gas having substantially no infrared absorptions in a specified wavelength range of interest. The method also includes the steps of taking a first spectral measurement from the sample cell and providing a biogas to the sample cell, the biogas comprising at least one siloxane compound. The method also includes taking a second spectral measurement from the sample cell, generating a first absorption spectrum based on a ratio of the first spectral measurement to the second spectral measurement and calculating a concentration of the at least one siloxane compound in the biogas by using the first absorption spectrum and a second absorption spectrum. The second absorption spectrum is based on, at least, an individual absorption spectrum for a known concentration of the at least one siloxane compound.

In some embodiments, the method includes performing, using a processor, a multiple regression analysis to calculate the concentration of at least one siloxane compound. Multiple regression analysis can be performed using Classical Least Squares (CLS), Partial Least Squares (PLS), Inverse Least Squares (ILS), or Principal Component Analysis (PCA).

The second absorption spectrum can be a model based on, at least, the individual absorption spectrum for the at least one siloxane compound and individual absorption spectra for one or more additional siloxane compounds, hydrocarbon compounds, water or carbon dioxide. In some embodiments, the second absorption spectrum is a model (e.g., a model representative of the individual absorption spectra of the agents in the biogas) based on known concentrations of the siloxane compounds, hydrocarbon compounds, water or carbon dioxide.

In some embodiments, a value for the concentration for the at least one siloxane compound is determined such that the second absorption spectrum (e.g., the model spectrum) is substantially similar to the first absorption spectrum (e.g., mathematically fitting the second absorption spectrum to the first absorption spectrum).

In some embodiments, the concentration of the at least one siloxane compound is calculated real-time (e.g., results of quantifying concentrations of siloxane compounds obtained in seconds or minutes) and in-situ (e.g., in-line or in a device in fluid communication with a source of the biogas and without the need for grabbing a sample).

The biogas can be provided from animal waste, wastewater or a landfill. In some embodiments, a turbine generator is shut off when the concentration of at least one siloxane compound reaches a threshold value.

In some embodiments, the second spectral measurement from the sample cell is taken in a wavelength range of about 8 microns to about 12 microns. The second spectral measurement can be taken over a 10 second acquisition time period. The second spectral measurement can be taken over different acquisition time periods (e.g., 1 second or greater or 100 seconds or less). In some examples, a typical range for acquisition time periods is between 10 seconds to 2 minutes. The step of taking the second spectral measurement comprises acquiring an infrared signal from the sample cell. The second absorption spectrum can be based on at least, an individual absorption spectra for L2-siloxane, L3-siloxane, L4-siloxane, L5-Siloxane, D3-siloxane, D4-siloxane, D5-Siloxane, D6-siloxane, Methane, Ethane, water, carbon dioxide, or an combination thereof.

In yet another aspect, the invention features a system for monitoring at least one siloxane compound in a biogas. The system includes a source of a first beam of radiation, an interferometer receiving the first beam of radiation from the source and forming a second beam of radiation comprising an interference signal and a sample cell in optical communication with the interferometer. The system also includes a flow mechanism establishing a first flow of a non-absorptive gas having substantially no infrared absorptions in a specified wavelength range of interest and a second flow of a biogas through the sample cell. A cooled detector is in optical communication with the sample cell, the cooled detector receiving a first interference signal propagating through the non-absorptive gas in the sample cell and a second interference signal propagating through a sample gas in the sample cell, the sample gas comprising the biogas. The system also includes a processor in electrical communication with the cooled detector, the processor configured to calculate a concentration of at least one siloxane compound in the biogas based on a first absorption spectrum based on ratio of the first interference signal to the second interference signal and a second absorption spectrum based on, at least, an individual absorption spectrum for a known concentration of the at least one siloxane compound. The system also includes a housing in which the source, the interferometer, the sample cell, the cooled detector and the processor are disposed.

In some embodiments, the sample cell includes a concave reflective field surface at a first end of the sample cell and a substantially spherical, concave reflective objective surface at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface.

In some embodiments, the second absorption spectrum is a model based on, at least, the individual absorption spectrum for the at least one siloxane compound and individual absorption spectra for one or more additional siloxane compounds, hydrocarbon compounds, water or carbon dioxide. The second absorption spectrum can be a model based on, at least, known concentrations of the siloxane compounds, hydrocarbon compounds, water or carbon dioxide.

In another aspect, the invention features a computer readable product, tangibly embodied on an information carrier or a machine-readable storage device, and operable on a digital signal processor for a biogas detection system. The computer readable product includes instructions operable to cause the digital signal processor to receive a first spectral measurement from a non-absorptive gas in a sampling cell, the non-absorptive gas having substantially no infrared absorptions in a specified wavelength range of interest. The product also includes instructions operable to cause the digital signal processor to receive a second spectral measurement from a sample gas comprising a biogas in the sampling cell, generate a first absorption spectrum based on a ratio of the first spectral measurement and the second spectral measurement, generate a second absorption spectrum based on, at least, a first individual absorption spectrum for a known concentration of at least one siloxane compound and perform a multiple regression analysis using the first absorption spectrum and the second absorption spectrum to calculate a concentration of the at least one siloxane compound in the biogas.

In some embodiments, the digital processor is configured to determine a value for the concentration of the at least one siloxane compound in the biogas such that the second absorption spectrum is substantially similar to the first absorption spectrum. The digital processor can be configured to generate the second absorption spectrum which is a model based on, at least, the first individual absorption spectrum and an individual absorption spectra for one or more additional siloxane compounds, hydrocarbon compounds, water or carbon dioxide.

The invention, in various embodiments, features a spectroscopic detection system for monitoring and/or detecting toxic chemical substances in a gas sample, such as ambient air. The system can be a compact, portable multiple gas analyzer capable of detecting and discriminating a broad range of chemical constituents including various chemical warfare agents (CWAs), toxic organic compounds (TOCs), and toxic industrial chemicals (TICs) at low or sub part per billion (ppb) levels. The system minimizes false alarms (e.g., false positives or false negatives), features high specificity, and can operate with response times on the order of a few seconds to a few minutes, depending on the application.

In one embodiment, the system can be packaged as an unobtrusive, automated unit capable of being deployed in an air handling system of a building to provide a rapid sensitive threat alert sufficient to protect building occupants and also allow adaptive infrastructure systems to react to the presence of a contaminant. In one embodiment, the unit is an entirely self-contained analyzer, with a FTIR spectrometer, a gas sample cell, a detector, an embedded processor, a display, an air pump, power supplies, heating elements, and other components onboard the unit with an air intake to collect a sample and an electronic communications port to interface with other devices.

In one aspect, the invention features an apparatus capable of measuring a trace gas. The apparatus includes a source of a first beam of radiation and an interferometer receiving the first beam of radiation from the source and forming a second beam of radiation including an interference signal. A sample cell is in optical communication with the interferometer, and the sample cell includes a concave reflective field surface at a first end of the sample cell and a substantially spherical, concave reflective objective surface at a second end of the sample cell. The objective surface and the field surface are in a confronting relationship, and the objective surface includes a cylindrical component increasing coincidence of foci in at least one plane to maximize throughput of the second beam of radiation propagating through the sample cell via multiple reflections on each of the field surface and the objective surface. The apparatus also includes a flow mechanism establishing a flow of a sample of gas through the sample cell, a cooled detector in optical communication with the sample cell, and a processor in electrical communication with the cooled detector. The cooled detector receives the interference signal propagating through the sample in the sample cell, and the processor determines from the interference signal an absorption profile for a trace gas in the sample. The source, interferometer, sample cell, cooled detector and processor can be disposed in a housing.

In another aspect, the invention features a method of optically measuring a trace gas. The method includes providing a portable absorption spectrometer including a sample cell having a field surface at a first end and an objective surface at a second end in a confronting relationship to form a folded path, and flowing a sample of ambient air through the sample cell. The volume of the sample cell and the number of passes of a beam of radiation in the folded path can be optimized to maximize throughput of the beam of radiation propagating in the sample cell to detect a trace gas having a concentration of less than about 500 ppb in the sample of ambient air.

In still another aspect, the invention features a method of optically measuring a trace gas. The method includes providing an absorption spectrometer including a sample cell that is substantially air tight. The sample cell includes a field surface at a first end and an objective surface at a second end in a confronting relationship to direct a beam of radiation through the sample cell. A first signal of the beam of radiation propagating through a sample of ambient air is measured at a first pressure in the sample cell. The sample cell is pressurized with ambient air to a second pressure, and a second signal of the beam of radiation propagating through the sample of ambient air at the second pressure is measured. The first signal and the second signal are combined to determine a signal indicative of the presence of a trace gas.

In various embodiments, the first signal and the second signal can be combined to determine an absorption profile for the trace gas. In some embodiments, the beam of radiation can include an interference signal. In one embodiment, an absorption profile for the trace gas can be determined from the interference signal propagating through the sample in the sample cell. In one embodiment, by pressurizing the sample cell, the amplitude of the absorption profile of the trace gas can be increased relative to a baseline signal.

In yet another aspect, the invention features a method of removing a contaminant from an optical system. The method includes a determining a concentration of a contaminant in at least a sample region of an absorption spectrometer and heating the sample region to a decontamination temperature to remove the contaminant if the concentration of the contaminant exceeds a contamination value The concentration of the contaminant is monitored while heating the sample region, and the heating of the sample region can be abated or ceased when the concentration of the contaminant reaches a decontamination value.

In still another aspect, the invention features an apparatus capable of measuring a trace gas. The apparatus includes an interferometer receiving the first beam of radiation from a source and forming a second beam of radiation comprising an interference signal, a sample cell in optical communication with the interferometer, a flow mechanism establishing a flow of a sample of gas through the sample cell, a module to heat at least the sample cell, a detector in optical communication with the sample cell, and a processor in electrical communication with the detector and the module. The detector receives the interference signal propagating through the sample in the sample cell. The processor determines from the interference signal a concentration of a contaminant in the sample, signals the module to heat the sample cell to a decontamination temperature to remove the contaminant if the concentration of the contaminant in the sample cell exceeds a contamination value, monitors the concentration of the contaminant while the module heats the sample cell, and signals the module to abate or cease heating the sample cell if the concentration of the contaminant reaches a decontamination value.

In other examples, any of the aspects above, or any apparatus or method described herein, can include one or more of the following features. In various embodiments, the trace gas has a concentration of less than about 500 ppb. In one embodiment, the trace gas has a concentration of between about 10 ppb and about 50 ppb. In one embodiment, the housing is portable and defines a hole for intake of ambient air comprising the sample of gas. The hole can be in fluid communication with the sample cell. In one embodiment, the sample cell can have a volume of less than about 0.8 liters. In some embodiments, the sample cell can have a pathlength of between about 5 meters and about 12 meters. In one embodiment, the apparatus also includes a heating element disposed in the portable housing to heat at least the sample cell to a temperature of between about 40° C. and about 180° C.

In some embodiments, the housing is mountable in an air handling system for a building. An alarm can sound to alert to the presence of a contaminant in the air handling system.

In one embodiment, the sample of gas flows through the sample cell at a rate of greater than about 3 liters per minute. The sample cell can have a gas exchange rate of between about 80% and about 95% in an interval of time of about 10 seconds. In one embodiment, the sample of gas includes a chemical warfare agent, a toxic inorganic compound, or a toxic organic compound. The apparatus can have a response time of less than about 20 seconds for about 50 ppb of a gas such as sarin, tabun, soman, sulfur mustard, or VX.

In various embodiments, a first absorption spectrum can be measured at a first resolution to detect the trace gas, and a second absorption spectrum can be measured at a higher resolution. In some embodiments, a first absorption spectrum can be measured at a first sensitivity to detect the trace gas, and a second absorption spectrum can be measured at a higher sensitivity.

In various embodiments, the field surface can include a concave reflective surface and the objective surface can include a substantially spherical, concave reflective surface. The objective surface can include a cylindrical component increasing coincidence of foci in at least one plane to maximize throughput of the beam of radiation propagating through the folded path of the sample cell. In one embodiment, an absorption profile for the trace gas can be determined from an interference signal propagating through the sample in the sample region.

Other aspects and advantages of the invention will become apparent from the following drawings, detailed description, and claims, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE INVENTION

Figure 1:
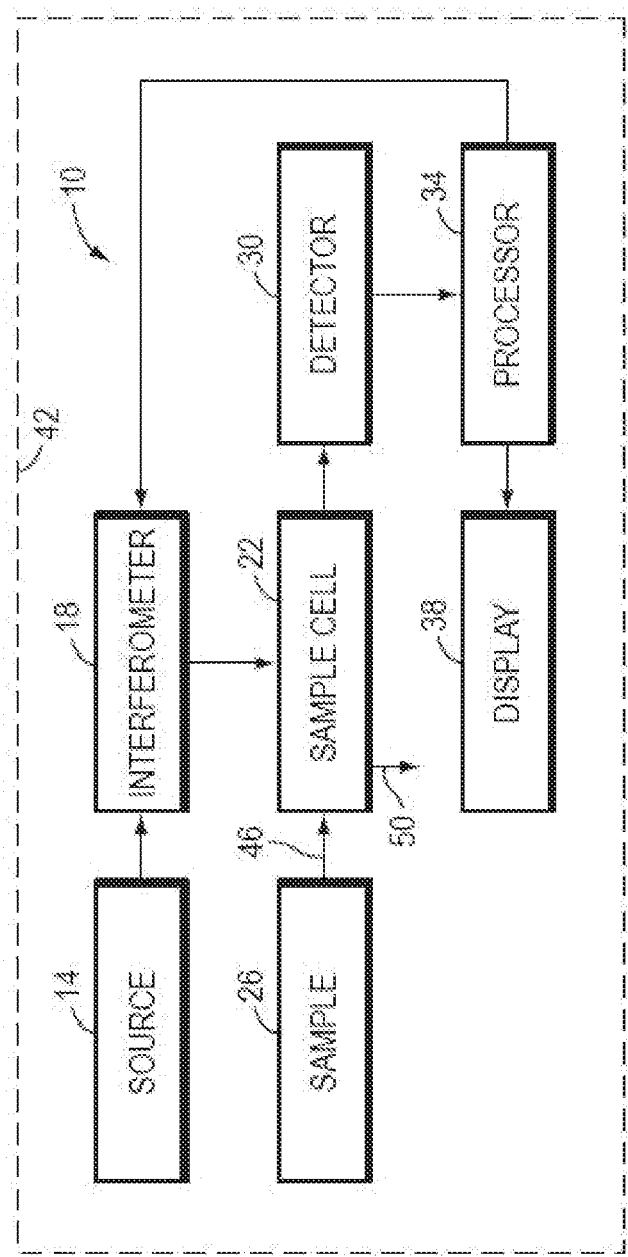
FIG. 1 depicts a block diagram of an exemplary detection system for monitoring and/or detecting a trace gas in a gas sample according to the invention.

FIG. 1 shows a block diagram of an exemplary apparatus 10 for monitoring and/or detecting a trace gas in a gas sample. The apparatus 10 can be used to detect trace amounts of substances such as sarin, tabun, soman, sulfur mustard, and VX nerve gas. The apparatus 10 can also be used, for example, to detect levels of siloxanes in a biogas. In some embodiments, vapors of a solid or liquid substance can be detected. The apparatus 10 can be an absorption spectrometer and/or can be a Fourier Transform Infrared (FTIR) spectrometer. In the embodiment illustrated, the apparatus 10 includes a source 14, an interferometer 18, a sample cell 22, a source for a gas sample 26, a detector 30, a processor 34, a display 38, and a housing 42. In various embodiments, the apparatus 10 can be used to detect a trace amount of a gas in a short period of time with few, if any, false positives or negatives.

In various embodiments, the source 14 can provide a beam of radiation (e.g., an infrared beam of radiation). The source 14 can be a laser or an incoherent source. In one embodiment, the source is a glowbar, which is an inert solid heated to about 1000° C. to generate blackbody radiation. The glowbar can be formed from silicon carbide and can be electrically powered. The spectral range of the system can be between about 600 $cm^{-1}$ and about 5000 $cm^{-1}$. The resolution of the system can be 2 $cm^{-1}$ and about 4 $cm^{-1}$. In one embodiment, the detection system can record a higher resolution spectrum of a trace gas upon detection of the trace gas. The higher resolution spectrum can aid identification of the trace gas.

In various embodiments, the source 14 of radiation and the interferometer 18 can comprise a single instrument. In some embodiments, the interferometer 18 is a Michelson interferometer, commonly known in the art. In one embodiment, the interferometer 18 is a BRIK interferometer available from MKS Instruments, Inc. (Wilmington, Mass.). A BRIK interferometer can include a combiner, which splits and combines incoming radiation, a moving corner cube to modulate the radiation, a white light source used to identify the center burst, and a Vertical Cavity Surface Emitting Laser (VCSEL) to monitor the velocity of the corner cube. The BRIK interferometer can be immune to tilt and lateral motion errors, as well as to thermal variations, which can enhance the ruggedness of the interferometer.

In one embodiment, the interferometer 18 can be a module including a source of radiation, a fixed mirror, a movable mirror, an optics module, and a detector module (e.g., the detector 30). The interferometer module can measure all optical frequencies produced by its source and transmitted through a sample (e.g., the sample 26 contained within the sample ell 22). Radiation is directed to the optics module (e.g., a beamsplitter), which can split the radiation into two beams, a first signal and a second signal. The movable mirror creates a variable path length difference between these two initially, substantially identical beams of electromagnetic energy. The movable mirror is normally moved or swept at a constant velocity. After the first signal travels a different distance (in this embodiment, due to movement of the movable mirror) than the second signal, the first and second signals can be recombined by the optics module, producing a radiometric signal with an intensity that is modulated by the interference of the two beams. This interference signal is passed through the sample and measured by the detector. The presence of different samples (e.g., a solid, liquid, or gas) can modulate the intensity of the radiation as detected by the detector. The output of the detector is, therefore, a variable, time-dependent signal depending upon the optical path difference established by the relative positions of the fixed mirror and the movable mirror, as well as the modulation of the electromagnetic signal produced by the sample. This output signal can be described as an interferogram.

The interferogram can be represented as a plot of received energy intensity versus position of the movable mirror. Those skilled in the art refer to the interferogram as a signal that is a function of time. The interferogram is a function of the variable optical path difference produced by the movable mirror's displacement. Since the movable mirror's position is normally and desirably swept at a constant velocity, those skilled in the art refer to the interferogram as a "time domain" signal. The interferogram can be understood to be a summation of all the wavelengths of energy emitted by the source and passed through the sample. Using the mathematical process of Fourier Transform (FT), a computer or processor can convert the interferogram into a spectrum that is characteristic of the light absorbed or transmitted through the sample. Because individual types of molecules absorb specific wavelengths of energy, it is possible to determine the molecule(s) present in the sample based on the interferogram and the corresponding spectrum. In a similar manner, the magnitude of the energy absorbed by or transmitted through the sample can be used to determine the concentration of a molecule(s) in the sample.

In various embodiments, an interferometer is not used to form an interference signal. An absorption spectrometer is used to record an optical signal, and information about the trace species is derived from the signal transmitted through the sampling region. For example, an absorption spectrum or a differential spectrum can be used.

In various embodiments, the sample cell 22 can be a folded path and/or a multiple pass absorption cell. The sample cell 22 can include an aluminum housing enclosing a system of optical components. In some embodiments, the sample cell 22 is a folded-path optical analysis gas cell as described in U.S. Pat. No. 5,440,143, the disclosure of which is herein incorporated by reference in its entirety.

In various embodiments, the source of the sample of gas 26 can be ambient air. The sample cell 22 or a gas sampling system can collect surrounding air and introduce it to a sampling region of the sample cell 22. The sample of gas can be introduced to the sample cell 22 at a predetermined flow rate using a flow system including an inlet 46 and an outlet 50 of the sample cell 22.

In various embodiments, the detector 30 can be an infrared detector. In some embodiments, the detector 30 is a cooled detector. For example, the detector 30 can be a cryogen cooled detector (e.g., a mercury cadmium telluride (MCT) detector), a Stirling cooled detector, or a Peltier cooled detector. In one embodiment, the detector is a deuterated triglycine sulfate (DTGS) detector. In one embodiment, the detector is a 0.5 mm Stirling-cooled MCT detector with a 16-μm cutoff, which can provide the sensitivity required for detecting a trace gas. The relative responsivity (i.e., ratio of responsitivity as a function of wavelength) of the Stirling-cooled MCT detector is at least 80% throughout the main wavelength region of interest (e.g., 8.3-12.5 μm). In addition, the D* value of the Stirling-cooled MCT detector can be at least $3 \times 10^{10}$ cm $Hz^{1/2}$ $W^{-1}$. The D* can be defined as the inverse of the detector noise equivalent power multiplied by the square-root of the active element area.

The processor 34 can receive signals from the detector 30 and identify a trace gas by its spectral fingerprint or provide a relative or absolute concentration for the particular material within the sample. The processor 34 can be, for example, signal processing hardware and quantitative analysis software that runs on a personal computer. The processor 34 can include a processing unit and/or memory. The processor 34 can continuously acquire and process spectra while computing the concentration of multiple gases within a sample. The processor 34 can transmit information, such as the identity of the trace gas, a spectrum of the trace gas, and/or the concentration of the trace gas, to a display 38. The processor 34 can save spectrum concentration time histories in graphical and tabular formats and measured spectrum and spectral residuals, and these can be displayed as well. The processor 34 can collect and save various other data for reprocessing or review at a later time. The display 38 can be a cathode ray tube display, light emitting diode (LED) display, flat screen display, or other suitable display known in the art.

In various embodiments, the housing 42 can be adapted to provide a detection system that is one or more of portable, rugged, and lightweight. The housing 42 can include a handle and/or can be readily secured to a transport mechanism, such as a pullcart or handtruck. The housing 42 can be rugged enough to resist misalignment of optics or breaking of components if transported and/or dropped. In various embodiments, the apparatus 10 can weigh as little as 40 pounds. In one embodiment, the apparatus 10 is entirely self-contained (e.g., includes all components in the housing 42 necessary to collect a sample, record a spectrum, process the spectrum, and display information relating to the sample).

Figure 2:
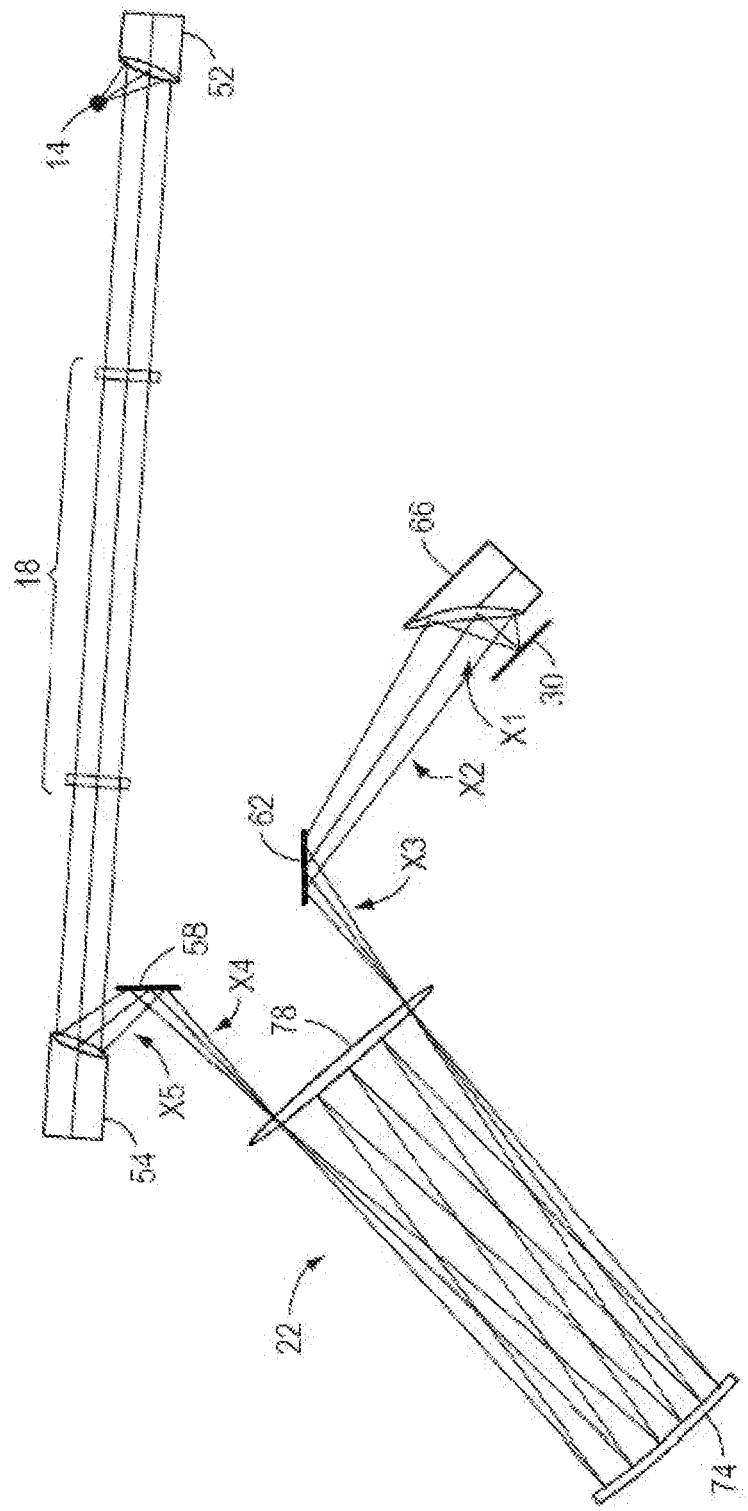
FIG. 2 shows a schematic diagram of an exemplary optical configuration according to the invention.

FIG. 2 shows an illustrative embodiment of an optical configuration that can be used with the apparatus 10. Radiation from the source 14 (e.g., a glowbar) is directed to the interferometer 18 (e.g., including a potassium bromide beamsplitter) by a first mirror 52. The beam of radiation is directed by a parabolic mirror 54 (PM) to a first folding mirror 58, and into the sample cell 22. The beam of radiation exits the sample cell and is directed by a second folding mirror 62 to a elliptic mirror 66 (EM), which directs the beam of radiation to the detector 30.

In one representative embodiment, the parabolic mirror 54 has an effective focal length of about 105.0 mm, a parent focal length of about 89.62 mm, and can have an off center value of about 74.2 mm. The diameter of the parabolic mirror 54 can be about 30.0 mm, and the angle of reflection can be about 45°.

In one embodiment, the elliptic mirror 66 can have a major semi axis of about 112.5, a minor semi-axis of about 56.09, and a tilt angle of the ellipse of about 7.11°. The diameter of the elliptic mirror 66 can be about 30.0 mm, and the angle of reflection (chief ray) can be about 75°.

In various embodiments, the first folding mirror 58 can have a diameter of about 25 mm, and the second folding mirror 62 can have a diameter of about 30 mm.

The mirrors and optics can include a gold coating, a silver coating, or an aluminum coating. In one embodiment, the elliptic and parabolic mirrors are coated with gold, and the flat folding mirrors are coated silver.

In various embodiments, the sample cell can include an objective surface 74 and a field surface 78. The objective surface 74 can be substantially spherical and concave. The field surface 78 can be concave, and positioned in a confronting relationship to the objective surface 74. The objective surface 74 can include at least one cylindrical component increasing coincidence of foci in at least one plane to maximize throughput of a beam of radiation propagating between the surfaces 74 and 78. In one embodiment, the objective surface 74 can include a plurality of substantially spherical, concave reflective objective surfaces, and each surface can include a cylindrical component increasing coincidence of foci in at least one plane to maximize throughput of the beam of radiation. The center(s) of curvature of the objective surface(s) can be positioned behind the field surface 78. By increasing coincidence of focus in at least one plane, distortion, astigmatism, spherical aberration, and coma can be better controlled, and higher throughput can be realized. Adding the cylindrical component can serve to reduce the effective radius of curvature in one plane, thus enabling light incident on the reflective surface to better approach the focus in the orthogonal plane. In one embodiment, the objective surface 74 has a cylindrical component superimposed thereupon providing different radii of curvature in two orthogonal planes. The objective surface 74 can have a contour that approaches toroidal.

The total pathlengths of the sample cell 22 can be between about 5 m and about 15 m, although longer and shorter pathlengths can be used depending on the application. In one detailed embodiment, the sample cell 22 has a total pathlength of about 10.18 m, resulting from a total number of passes of about 48 between the objective surface 74 and the field surface 78. The optics of the sample cell 22 can be optimized for 0.5-mm detector and a 1 steradian collection angle. The detector optic magnification ratio can be about 8:1. The objective surface 74 and the field surface 78 can have a gold coating with a nominal reflectance of about 98.5% between 800-1200 $cm^{-1}$. The internal volume of the sample cell can be between about 0.2 L and about 0.8 L, although larger and smaller volumes can be used depending on the application. In one detailed embodiment, the volume is about 0.45 L.

In one embodiment, the mirrors and optics used to direct the beam of radiation into and through the sample cell 22, to focus the beam of radiation on an entrance slit of the sample cell 22, and/or to direct the beam of radiation to the detector can be optimized to match the sample cell's optical characteristics, which can maximize throughput of radiation and enhance sensitivity of the detection system.

For example, in one embodiment, an optical configuration properly aligned can have an efficiency of about 88.8%. As used herein, the efficiency can be the ratio of number of rays impinging the image square to the total number of emitted rays within the angular range of emission. In one embodiment, the position of the folding mirrors 58 and 62 and the detector 30 can be adjustable, which allows one to compensate for various mechanical tolerances errors between the interferometer 18, the parabolic mirror 54, the sample cell 22, and the detector 30. In one embodiment, the following nominal (designed) optical distances can be used to optimize throughput.

Detector to elliptic mirror (X1) of about 21.39 mm.
Elliptic mirror to folding mirror (X2) of about 132.86 mm.
Folding mirror to sample cell (surface of the field mirror) (X3) of about 70.00 mm.
Sample cell path length of about 10181.93 mm.
Sample cell to folding mirror (X4) of about 70 mm.
Folding mirror to parabolic mirror (X5) of about 35 mm.

Figure 3:
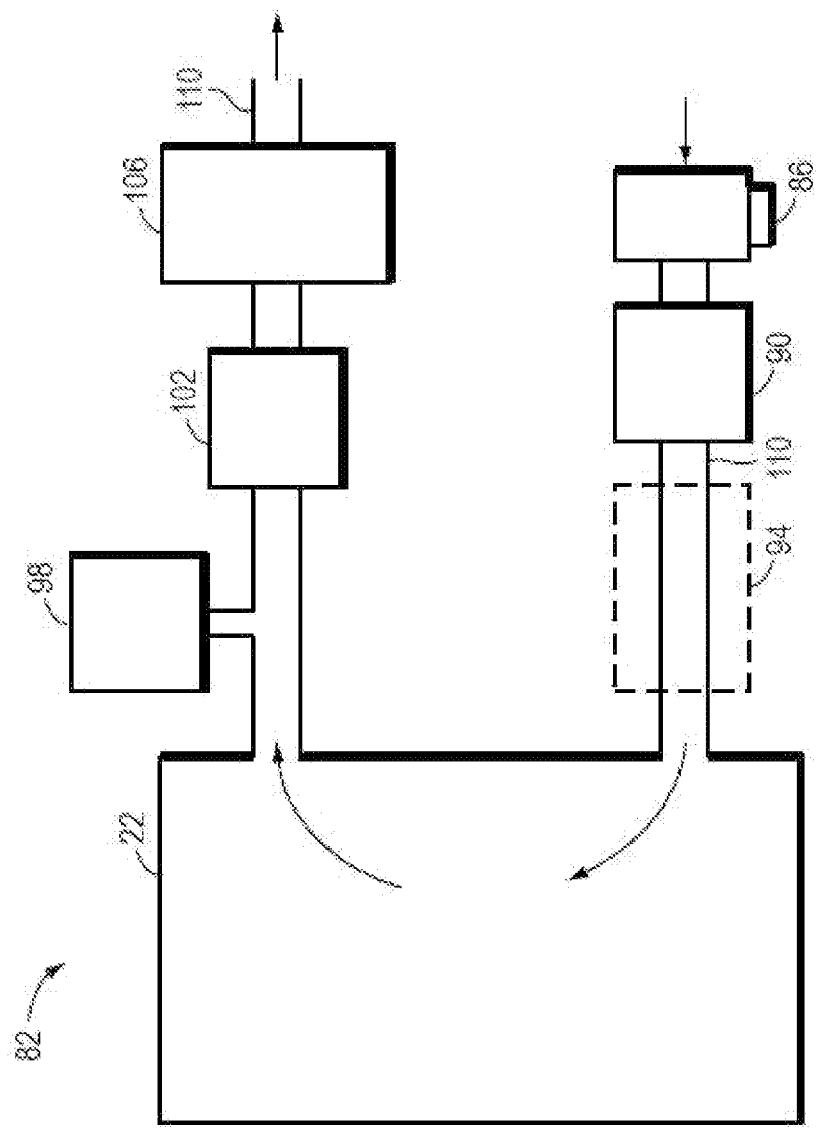
FIG. 3 shows a block diagram of an exemplary flow system for introducing a sample into a sample cell according to the invention.

FIG. 3 shows an illustrative embodiment of an exemplary flow system 82 for introducing a sample to the sample cell 22. The flow system 82 includes a filter 86, a flow sensor 90, an optional heating element 94, the gas cell 22, a pressure sensor 98, a valve 102, and a pump 106 connected by gas lines 110. Arrows show the direction of flow. One or more of the flow system 82 components can include wetted parts, such as, for example, Teflon, stainless steel, and Kalrez, to withstand decontamination temperatures and to resist the corrosive nature of CWAs and TICs.

The filter 86 can be an inline 2 µm stainless steel filter available from Mott Corporation (Farmington, Conn.). The flow sensor 90 can be a mass flow sensor including stainless steel wetted parts, e.g., a flow sensor available from McMillan Company (Georgetown, Tex.). The heating element 94 can be line heaters available from Watlow Electric Manufacturing Company (St. Louis, Mo.). The pressure sensor 98 can be a Baratron pressure sensor available from MKS Instruments (Wilmington, Mass.). The valve 102 can be stainless steel and include a Teflon o-ring, e.g., a valve available from Swagelok (Solon, Ohio). The gas lines 110 can be ⅜" diameter tubing available from Swagelok.

The pump 106 can be a "micro" diaphragm pump with a heated head. A Dia-Vac B161 pump available from Air Dimensions, Inc. (Deerfield Beach, Fla.) can be used. In one embodiment, a miniature diaphragm pump available from Hargraves Technology Corporation (Mooresville, N.C.) can be used. In the illustrative embodiment, the pump 106 can be positioned downstream from the sample cell 22 to draw air through it. As a result, any leakage in the system can be pulled away from, instead of pushed into, the analyzer to minimize the risk of contaminating the internal components of the analyzer. In addition, an unwanted product of an unintended chemical reaction involving elastomers of the pump can be prevented from entering the sample cell 22.

In various embodiments, the rate of flow through the flow system 82 can be between 2 L/min and 10 L/min, although larger and smaller flow rates can be used depending on the application. In one embodiment, the flow rate is between 3 L/min and 6 L/min. The pressure of the sample can be about 1 atm, although larger and smaller pressures can be maintained depending on the application. In some embodiments, the sample cell can be operated an elevated pressures, such as up to 4 atm. The operating temperature of the sample cell can be between about 10° C. and of about 40° C., although larger and smaller temperatures can be maintained depending on the application. In one embodiment, the detection system can include a heating element to heat the sample to between about 40° C. and of about 180° C. In one embodiment, the temperature can be increased up to about 150° C. to decontaminate the apparatus.

In various embodiments, the sample cell pathlength can be between about 5 m and about 12 m. The spacing between the field surface and the objective surface can be constrained by the gas sampling flow rate. In one embodiment, a 5.11-meter sample cell with 16 cm spacing and 32 passes can have an internal volume of about 0.2 L. In another embodiment, For the same number of passes, a 20.3 cm spacing with 32 passes can have a volume of about 0.4 L. In yet another embodiment, a 25.4 cm spacing can have a volume of about 0.6 L. A flow rate can be determined that can provide an adequate supply of "fresh" ambient gas at least every 10 seconds, although smaller sampling rates can be attained. In various embodiments, the rate of flow (e.g., between 2 L/min and 10 L/min) can be optimized to provide an optimal exchange rate of gas. For example, in one embodiment, the exchange rate of gas is at least 80% in a detection time interval of 20 seconds. In one embodiment, the gas exchange rate of is between about 80% and about 95% in a detection time interval of 10 seconds.

Pathlength/NEA ratio can be used as a metric for quantifying a detection system's sensitivity, where pathlength is the total beam path length of the sample cell measured in meters and NEA is the noise equivalent absorbance measured in absorbance units (AU). Provided that the sensitivity is limited by detection system's non-systematic errors (also called random noise, such as detector and electronic noise), the detection limit can be inversely proportional to the Pathlength/NEA ratio. For example, if the ratio were doubled, the detection limit of a particular sample in ppb or $mg/m^3$ would be halved. It is thus an appropriate quantification metric for the sensitivity performance. This metric does not take into account sensitivity enhancement due to advanced sampling techniques, such as, for example, gas pressurization and cold trapping.

Taking into account the limiting system noise, such as detector and digitization noise, Pathlength/NEA ratio can be optimized for various system configurations. Parameters that can be optimized include flow rate, sample cell volume, optical pathlength, number of passes through the sample cell, optical configuration, mirror reflectivity, mirror reflective material, and the detector used. For example, an optimum detector is one that has the highest D* value and speed (lower response time), within the constraints of size, cost and service life.

For a detector noise limited spectrometer, the sensitivity or Pathlength/NEA ratio is proportional to the D* value. Detector bandwidth can determine the maximum scan speed, which in turn determines the maximum number of data averaging that can be performed within the allowed measurement period. For a detector or electronic noise limited system, sensitivity generally increases with the square root of the number of averaged scans or, for example, the time to perform these scans. In one embodiment, a Stirling-cooled detector can provide a Pathlength/NEA sensitivity ratio of at least $1.5 \times 10^5$ m/AU. A DTGS detector can provide an inexpensive alternative due to its low cost and maintenance-free life, although it can have a lower D* value and be slower.

Figure 4:
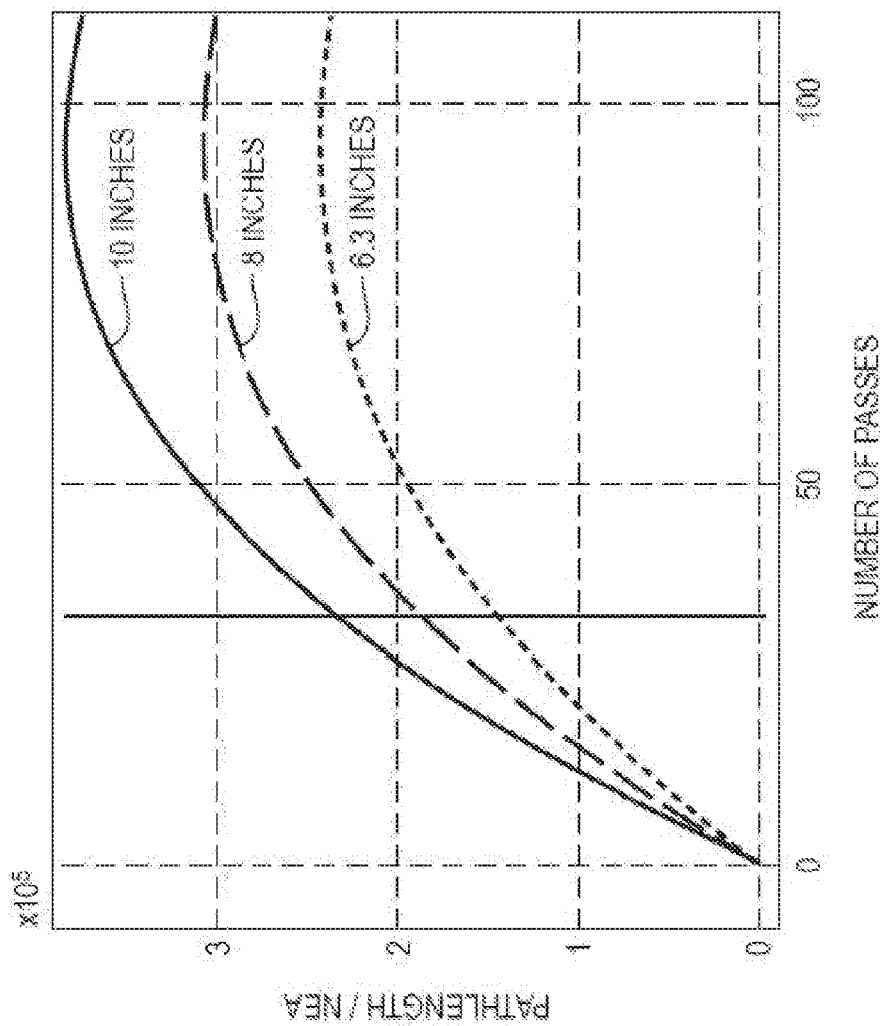
FIG. 4 is a graph of pathlength/NEA versus number of passes between optical surfaces of a sample cell according to the invention.

The Pathlength/NEA value can be determined by optimizing the distance between the field surface and the objective surface and the number of passes between these surfaces. FIG. 4 shows a graph of Pathlength/NEA as a function of mirror reflections for various surface spacings, e.g., 6.3 inches (16.0 cm), 8 inches (20.3 cm) and 10 inches (25.4 cm). As shown in FIG. 4, the maximum Pathlength/NEA values occur at about 92 passes. At 92 passes, only 25% of the light is transmitted due to reflection losses at the mirror surfaces, however. In one detailed embodiment, a sample cell has a transmittance of between about 50% and about 60%. With mirror reflectance of 98.5%, a 60% transmittance corresponds to about 32 passes, which is represented by the vertical line in FIG. 4. A 50% transmittance corresponds to about 48 passes. Table 1 shows exemplary combinations of parameters for providing a sampling system for detecting a trace gas in a sample.

TABLE 1

Exemplary combinations of parameters for providing a sampling system for detecting a trace gas in a sample.

| System | Surface spacing (cm) | Number of passes | Total pathlength (m) | Pathlength/ NEA (m/AU) | Cell volume (L) | Flow rate[1] (L/m) | Flow rate[2] (L/m) |
| --- | --- | --- | --- | --- | --- | --- | --- |
| A | 16.0 | 32 | 5.11 | $1.4 \times 10^5$ | 0.2 | 2 | 3 |
| B | 20.3 | 32 | 6.5 | $1.8 \times 10^5$ | 0.4 | 4 | 6 |
| C | 25.4 | 32 | 8.1 | $2.3 \times 10^5$ | 0.6 | 6 | 9 |
| D | 16.0 | 48 | 7.7 | $1.9 \times 10^5$ | 0.3 | 3 | 4.5 |
| E | 21.1 | 48 | 10.18 | $2.5 \times 10^5$ | 0.5 | 5 | 7.5 |
| F | 25.4 | 48 | 12.2 | $3.0 \times 10^5$ | 0.8 | 8 | 12 |

[1] Flow rate for a gas exchange rate of 80% at an interval of 10 seconds.
[2] Flow rate for a gas exchange rate of 90% at an interval of 10 seconds.

The Pathlength/NEA ratio can be translated to detection limits in $mg/m^3$ or parts per billion (ppb) of concentration. A method used for such a translation is a comparison between the expected peak absorbance magnitude and the expected NEA value. The apparatus 10 can be used to detect trace amounts of a substance such as sarin, tabun, soman, sulfur mustard, and VX nerve gas with a concentration lower than about 500 ppb. In various embodiments, the concentration can be between about 10 ppb and about 500 ppb, although higher and lower concentrations can be detected depending on the system and the application. In some embodiments, the concentration can be between 5 ppb and about 50 ppb, depending on the species. For example, the apparatus 10 is capable of detecting a trace amount of sarin with a concentration of between about 8.6 ppb and about 30 ppb; a trace amount of tabun with a concentration of between about 12.9 ppb and about 39 ppb; a trace amount of tabun with a concentration of between about 7.3 ppb and about 22.8 ppb; a trace amount of sulfur mustard with a concentration of between about 36.7 ppb and about 370.6 ppb; or a trace amount of VX nerve gas with a concentration of between about 12.9 ppb and about 43.9 ppb.

Gas renewal rate, which is a measure of the build-up of a fresh gas supply in a sample cell, can be coupled with the Pathlength/NEA ratio, resulting in a detection system response time specified as "X $mg/m^3$ (or ppb) of gas Y detected in Z seconds". The detection system response time includes the measurement time and the computation time (e.g., about 5 seconds). Table 2 shows exemplary detection system response times for various agents such as sarin, tabun, soman, sulfur mustard, and VX nerve gas.

TABLE 2

Exemplary detection system response times for trace gases measured using a detection system of the invention.

| Trace gas | Response time for 10 ppb | Response time for 20 ppb | Response time for 30 ppb | Response time for 50 ppb |
| --- | --- | --- | --- | --- |
| Sarin | 15.4 | 12 | 8.7 | 7.5 |
| Tabun | 22.6 | 12.6 | 10.2 | 8.4 |
| Soman | 13.7 | 9.6 | 8.3 | 7.2 |
| Sulfur mustard | 60 | 37.5 | 21.4 | 13.8 |
| VX nerve gas | 22.6 | 12.6 | 10.2 | 8.4 |

All response times are in seconds.

Figure 5:
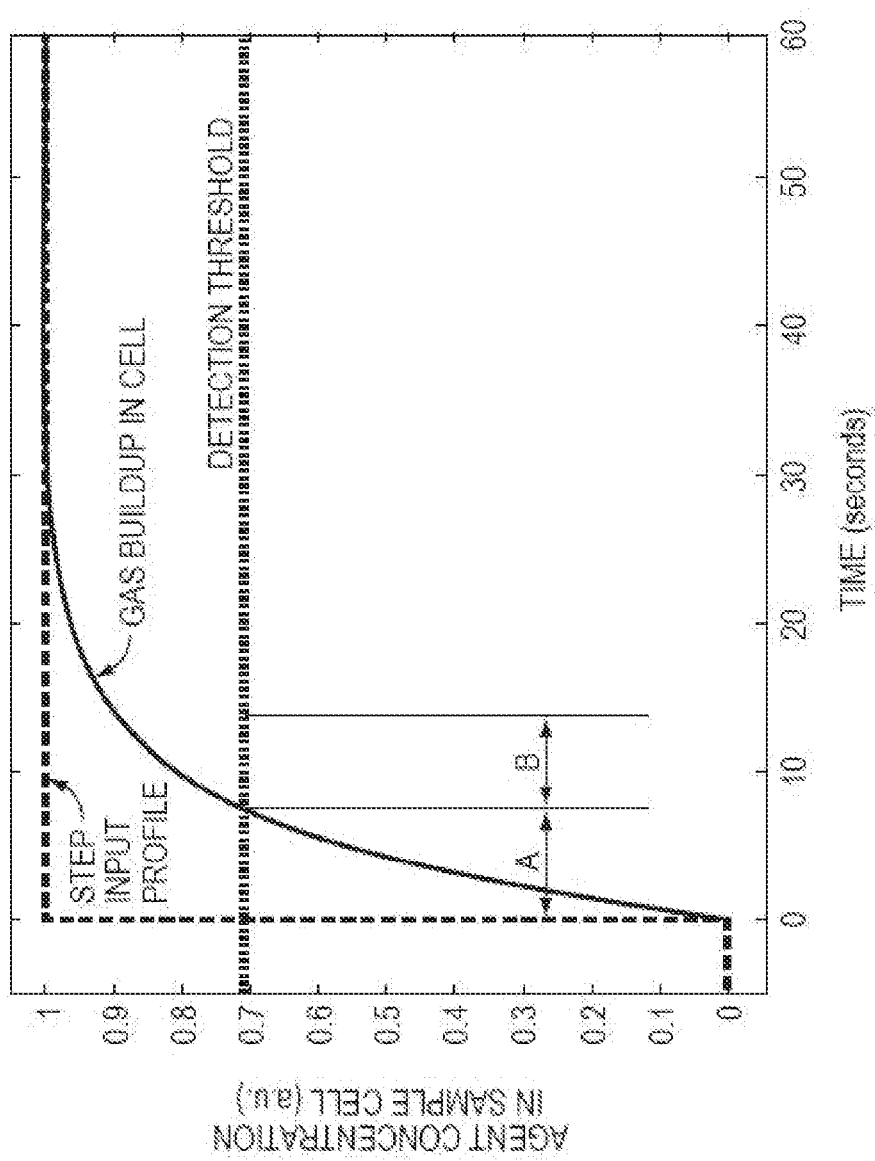
FIG. 5 is a graph of concentration of a trace gas versus time during input of the trace gas into an exemplary detection system according to the invention.

FIG. 5 is a graph of concentration of a trace gas versus time using a step profile input (e.g., the trace gas enters the sample cell at the beginning of the measurement cycle). The measurement period "A" is the time when data is collected and/or an interferogram is recorded. The computation period "B" is when the interferogram is converted to a spectrum, and a spectral analysis is performed to produce data from which alarm levels and/or concentration values can be determined.

Figure 6:
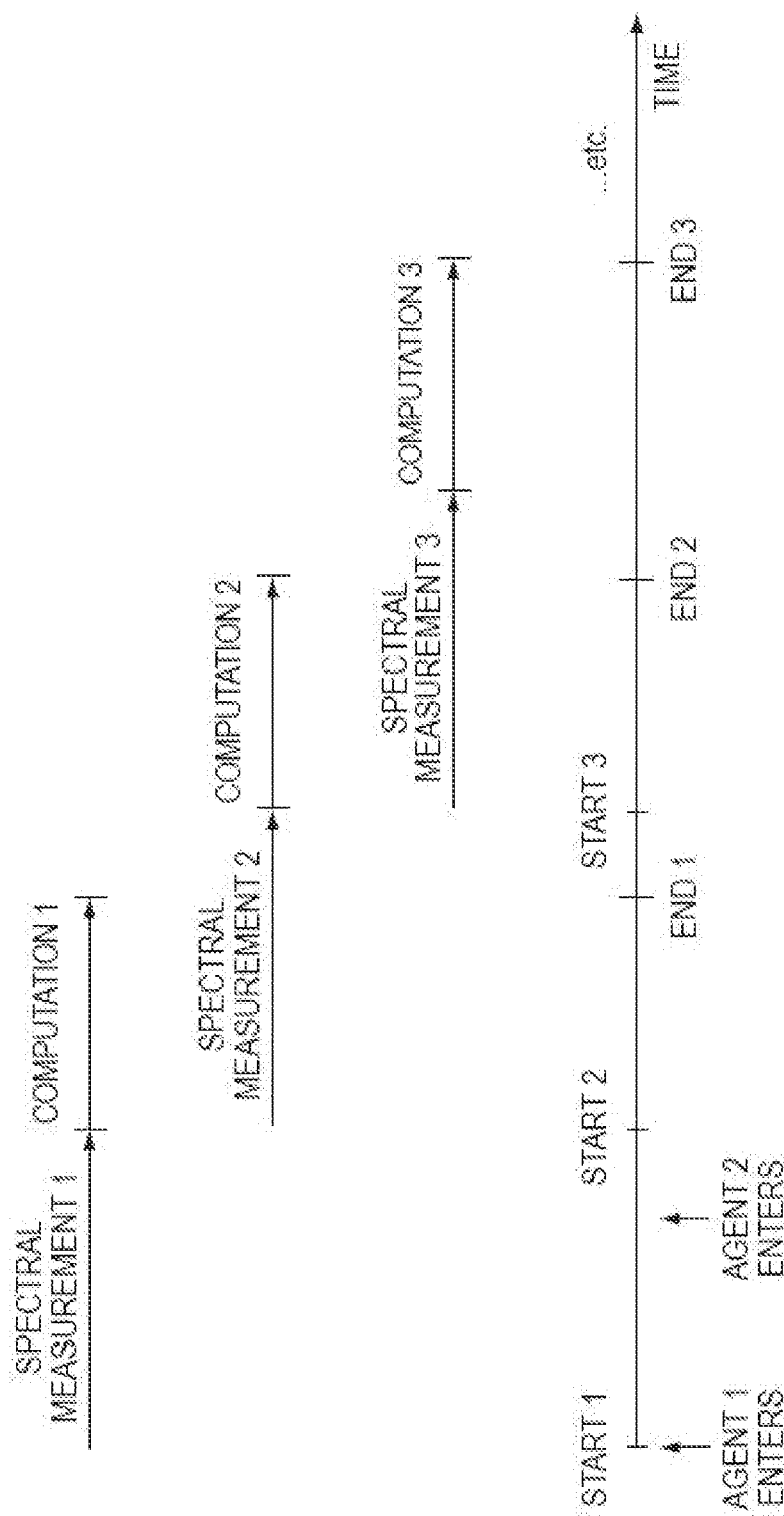
FIG. 6 shows a timeline for a series of measurements according to the invention.

FIG. 6 shows a timeline for a series of measurements. Agent 1 enters the sample cell and is detected during measurement period 1. An interferogram is analyzed during computation period 1. Agent 2 enters the sample cell during measurement period 1. If agent 2 is sufficiently strong, it can be detected during the remaining portion of measurement period 1. If agent 2 is not detectable, then it is detected during a subsequent measurement period, e.g., measurement period 2, and an interferogram is analyzed during the succeeding computation period, e.g., computation period 2.

In one embodiment, readings can be separated temporally with a fixed predetermined interval. In various embodiments, the interval can be between about 1 second and about 1 minute, although smaller or larger intervals can be used depending on the application. In some embodiments, the interval is about 5 seconds, about 10 seconds, or about 20 seconds. The response time, therefore, depends on this interval as well as when then agent is detectable by the detection system.

In various embodiments, the detection system can adapt one or more parameters based on an external factor, such as detection of a trace gas, a threat level, the time of day, the number of people in a room or building that can be affected by the agent, a particular measurement application or scenario, or a combination of the aforementioned. For example, in a high-threat condition, a smaller interval can be used to minimize detection time and maximize detectability of a trace agent. In a low threat situation, a larger interval can be used, which can preserve the detection systems lifetime and reduce the likelihood of a false alarms (either false positives or false negatives).

Furthermore, an individual measurement that exceeds a threshold level for a particular agent can trigger the detection system to decrease the interval so that additional measurements can be made in a shorter amount of time. In various embodiments, a first spectrum can be recorded at a first resolution or sensitivity. If a contaminant is detected, a second spectrum can be recorded at a higher resolution or sensitivity, respectively. Furthermore, the detector can have a standby mode, in which it operates at a higher temperature, thereby decreasing its sensitivity. When triggered by the external factor, the temperature of the detector can be decreased to improve its sensitivity.

In various embodiments, the detection system can change the number of scans based on an external factor or a perceived threat. For example, an increased number of scans can be performed to enhance the sensitivity of the detection system. In one embodiment, the detection system can operate at higher resolution while recording these additional scans. In one embodiment, each scan can include an increased number of averages or individual scans.

In various embodiments, the detection system only digitizes a low frequency region (e.g., lower than 1300 cm$^{-1}$) of the spectrum, so that the detection system can scan at a faster rate. An electronic filter or detector response function can be used to remove a higher frequency region (e.g., greater than 1300 cm$^{-1}$) so that aliasing can be prevented or minimized.

In some embodiments, the detection system can detect the presence of a trace gas in one portion of the spectrum. A second portion of the spectrum can be analyzed to confirm the presence of the trace gas and/or determine the trace gas's concentration level.

Figure 7:
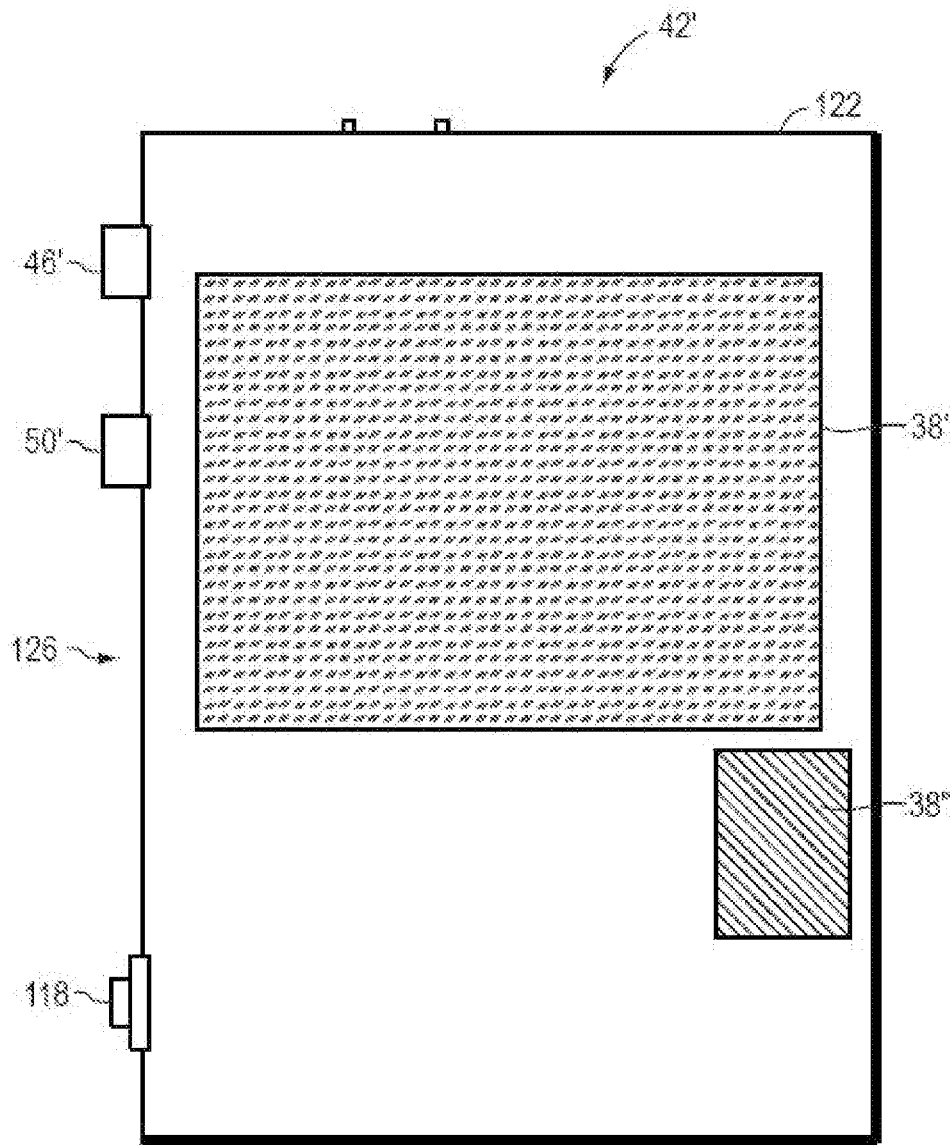
FIG. 7 depicts a plan view of an exemplary detection for monitoring and/or detecting a trace gas in a gas sample according to the invention.
Figure 8:
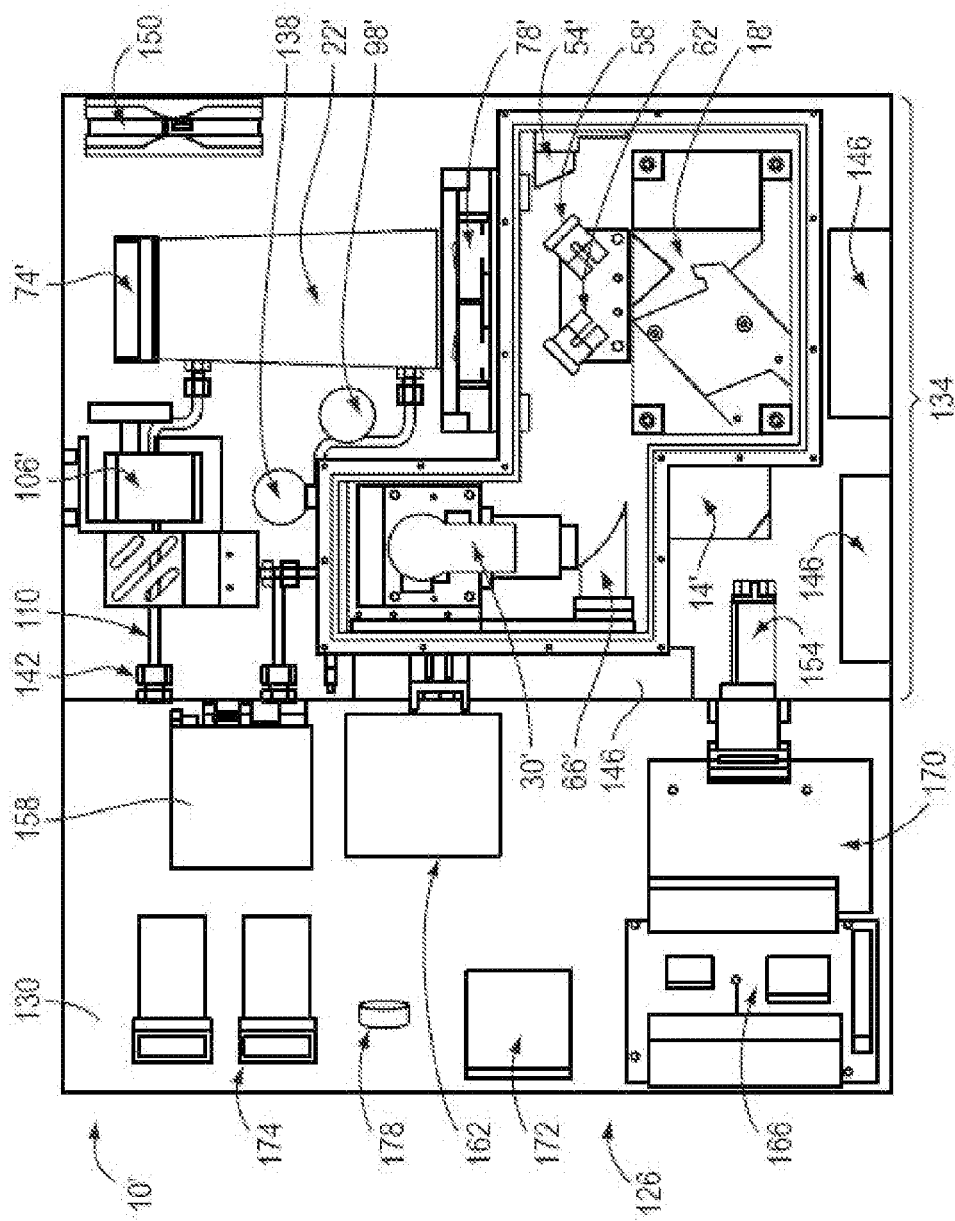
FIG. 8 shows a plan view of some components of an exemplary detection for monitoring and/or detecting a trace gas in a gas sample according to the invention.

In one embodiment, the detection system can be packaged as a compact, self-contained multiple gas analyzer. For example, the detection system can be a diagnostic tool for recording, charting, analyzing, and reporting air quality. FIGS. 7 and 8 shows an exemplary detection system for monitoring air quality, e.g., ambient air for trace gases. Referring to FIG. 7, the detection system includes a housing 42', a first display 38', a second display 38", a gas inlet 46', a gas outlet 50', and a port 118 for connecting to external devices.

The housing 42' can be a three-dimensional rectangular box including a top panel 122, side panels 126, and a bottom panel 130 (shown in FIG. 8). The top panel 122 can be hinged off a side panel 126, so that the housing 42' can be opened for service. The external surface of the top panel 122 can include the first display 38' and the second display 38" attached thereto or embedded therein. The first display 38' can be a liquid crystal display (LCD), for example, with a touchscreen display. The first display 38' can receive commands for operating the detection system and can display a graphical user interface (GUI). The second display 38" can be a light emitting diode (LED) display, for example, with a series of LEDs that light up to indicate a threat level, alarm status, and/or detection system health status. For example, the second display 38" can include a first series of green, yellow and red LEDs to indicate an alarm status, and a second series of green, yellow and red LEDs a separate to indicate sensor health status. In various embodiments, the housing 42' can define a hole for intake of ambient air. The hole can be used to introduce the sample of gas into the flow system for detection in the sample cell.

FIG. 8 shows internal views of the top panel 122 and the bottom panel 130 when the top panel 122 is hinged open. The bottom panel includes an internal chassis including an optics box 134 for housing optical components. The optics box 134 can be formed from an aluminum shell (e.g., 6061-T6). In one embodiment, the optics box 134 is a hermetically sealed box. As illustrated in FIG. 8, the optics box 134 includes a source 14', an interferometer 18', a sample cell 22', a detector 30', a parabolic mirror 54', a first folding mirror 58', a second folding mirror 62', an elliptic mirror 66', an objective surface 74', and a field surface 78'. The optics box 134 also can include a flow system including a valve 138 to regulate gas flow, a pressure sensor 98', a pump 106', and gas lines 110 and fittings 142 for making connections. Power supplies 146 for various components and a fan 150 can also be attached to the bottom panel 130. The detection system can be operated in still air, and fans 150 can maintain the internal temperature of the system. The bottom panel 130 also includes a connector 154 to interface with the top panel 122.

As illustrated in FIG. 8, the top panel 122 can include electronic components attached thereto. For example, the top panel 122 can include a data acquisition module 158, a mirror motion control module 162, a single board computer 166, a power distribution module 170, and a hard drive 172. The data acquisition module 158 can include a preamplifier, an analog-to-digital converter, and a data acquisition board. The preamplifier can amplify an analog signal received from the detector 30'. The analog signal can be converted to a digital signal using the analog-to-digital converter. The data acquisition board can be a Netburner processor board available from Netburner (San Diego, Calif.). The single board computer 166 can be an off the shelf PC motherboard running Windows and presenting a GUI to a user.

The power distribution module 170 can handle and distribute power to other modules in the system, and can implement health and status sensors used to monitor the detection system's functionality. For example, the power distribution module 170 can distribute AC power to system power supplies 146 and fans 150, and can control temperature controllers 174, e.g., Love Controls available from Dwyer Instruments, Inc. (Michigan City, Ind.). The power distribution module 170 also monitors sample cell pressure, differential pressure across the air filter, sample cell temperature, and detector temperature, A/D converts the outputs, and communicates the results back to the single board computer 166. The power distribution module 170 also can control a Stirling cooled detector's cooler motor under command from the single board computer 166. The top panel 122 also can include sample cell temperature transmitter.

Data processing can be performed using the modules attached to the top panel 122, which can enable real time analysis of data. The spectral library can include spectral fingerprints of between about 300 and about 400 gases, although more gases may be added as spectra are recorded. Data processing can be performed with a standard computer programming language, such as MATLAB or C++. The spectra recorded can be transferred to MATLAB for spectral post-processing to compute gas concentrations, spectral residuals, and/or false alarm rates. In various embodiments, the detection system can operate with fewer than about six false alarms per year. False alarms can result from noise, anomalous spectral effects, analysis code, model errors, errors in spectral library, or an unknown interferent.

The computer software can operate on a Java based platform with graphical remote control capability. It can incorporate standard services including user login, web-based GUI, alarm triggering, and/or an Ethernet interface to a client computer that may be located remote from the detection system. The computer software can perform remote health and control diagnostics. In addition, the port 118 can be used to connect the system to a stand alone computer, which can perform data processing and data analysis.

The housing 42' is designed to withstand a 50 G shock. In one embodiment, the housing 42' can have a length of about 406 mm and a width of about 559 mm. The mass the detection system can be about 20 kg. The housing 42' can be mountable on a wall, on a movable cart, or on a handtruck, and can include a handle (not shown) for carrying, either manually or using a mechanical lifting apparatus. In one embodiment, the housing can be mounted as part of an air handling system for a building. When the detector senses the presences of a contaminant, remedial measures can be taken to account for the contaminant. For example, an alarm can sound to evacuate the building, or air flow in the air handling system can be increased to sweep the contaminant away from a public area or to dilute the trace gas to an acceptable level.

In various embodiments, the detection system can be operated at an elevated temperature to decontaminate the system in the event of contamination. The system can be configured so that the sample cell and flow system can be heated to a temperature of between about 150° C. and about 200° C., while the remaining components including electronics and optical components are maintained at a temperature below about 70° C. For example, the components being heated to about 150° can be insulated from the surrounding components to prevent damage of electronics and realignment or damage of optical components. Operation of the sample cell and flow system at an elevated temperature can speed up desorption of the contaminant. In one embodiment, the detection system can be operated while the system is being decontaminated, so that progress of the decontamination can be monitored. In one embodiment, the detection system is purged with nitrogen gas or ambient air during decontamination. The gas can include moisture (e.g., a relative humidity of greater than or equal to about 30%). In various embodiments, the system can be decontaminated in less than about 2 hours and be ready to be returned to service.

In one embodiment, a concentration of a contaminant in a detection system can be determined, and if the concentration of the contaminant exceeds a contamination value, at least the sample region can be heated to a decontamination temperature to remove the contaminant. The concentration of the contaminant can be monitored while heating the sample region, and when the concentration of the contaminant reaches a decontamination value, the heating can be abated or ceased. The contamination value can be a concentration of a substance that inhibits the performance of the detection system. The decontamination value can be a concentration of the substance at which the detection system can be operated without influence from the contaminant.

In various embodiments, the sample cell of the detection system can be operated at elevated pressure. Although the Pathlength/NEA ratio may not change, the sensitivity of the detection system can be enhanced as a larger amount of a trace gas sample can be present in a sample cell having the same pathlength. This, in turn, can generate a larger absorption signal, relative to the baseline. The pressure can be elevated by increasing the flow rate while keeping the sample cell volume unchanged.

The field surface and the objective surface can be fixably mounted so that their position remains substantially unchanged when the pressure is elevated. For example, the field surface and the objective surface can be mounted on rods to hold these surfaces. In addition, the sample cell can be substantially air tight. The objective surface and the field surface in the sample cell can be bathed in the sample gas so that a positive pressure can be applied to a back surface of each of the field surface and the objective surface to prevent deformation at elevated pressure. In various embodiments, the pressure can be between 1 atm and about 10 atm. In one embodiment, the pressure is 4 atm.

In some embodiments, signals at two distinct pressures can be measured and a ratio of these signals can be taken. The ratio of signals can remove baseline noise, enhance sensitivity, and/or increase the amplitude of the absorption profile of the trace gas relative to the baseline signal.

A first signal of a beam of radiation propagating through a sample of ambient air at a first pressure in the sample cell is measured. The sample cell is pressurized with ambient air to a second pressure. A second signal of the beam of radiation propagating through the sample of ambient air is measured at the second pressure in the sample cell. The first signal and the second signal can be combined to determine a signal indicative of the presence of a trace gas. For example, the signals can be combined to yield an absorption profile for the trace gas. In one embodiment, the beam of radiation can include an interference signal. The absorption profile for the trace gas can be determined from the interference signal. In one embodiment, the first pressure is about 1 atm, and the second pressure is between about 1 atm and 10 atm. In one detailed embodiment, the first pressure is about 1 atm, and the second pressure is about 4 atm.

In various embodiments, the first signal is used as a baseline signal for the second signal because the optical alignment of the sample cell remains substantially unchanged when the pressure is increased. In some embodiments, a baseline signal is measured and used as the baseline signal for both the first signal and the second signal.

In various embodiments, the flow system can include a cold finger to trap a gaseous sample of interest by cooling it down below its saturation temperature. Many volatile materials condense at or below a temperature of −75° C. In one embodiment, a cryogenic cold trap is established in the gas outlet from the sample cell. After a specified period of time or collection period, a trapped gas or trapped gases can be rapidly vaporized or "flashed" back into the sample cell by heating them up, and a spectral measurement can be made. This technique can increase the amount of a target gas by about an order of magnitude or two, while maintaining the sample cell at atmospheric pressure. In one embodiment, continuous flow measurements are performed after an interval of time, e.g., about every 10 seconds, while flashing occurs at a longer time interval.

In various embodiments, the detection system can include a long-wave-pass filter. Noise due to the A/D converter can be on the same order of magnitude with the noise due to the detector. Incorporating a long-wave-pass filter can block the higher wavenumber region, and can improve sensitivity by reducing the digitizer dynamic range requirement through reduction of the interferogram centerburst magnitude. The dynamic range of a detector without an optical filter can be between about 600 $cm^{-1}$ and about 5000 $cm^{-1}$. Since many of the toxic substances targeted are detectable below 1500 $cm^{-1}$, the spectrum higher than 1500 $cm^{-1}$ can be eliminated using a long-wave-pass filter to gain sensitivity. For example, with a standard off-the-shelf long-wave-pass filter with a cut-off at about 1667 $cm^{-1}$, the gain in Pathlength/NEA ratio can be about 20% to about 30%. In addition, using a long-wave-pass filter can improve a detection system's signal-to-noise ratio by allow a detector to be operated at higher gain, e.g., the highest gain achievable with a particular detector. In various embodiments, a low sensitivity detector, such as a MCT detector or a DTGS detector, can be used to record a spectrum in a higher frequency region.

Biofuels can be used to power engines for turbine generators. Biogases generally include species such as, for example, hydrocarbons (e.g., $CH_4$) with percentage levels of $CO_2$ and $H_2O$. Biogases also include siloxane compounds. Cyclic siloxanes (e.g., D3-siloxanes to D6-siloxanes) can be found in biogas produced by a digester. Biogases from landfills can include linear siloxanes (e.g., "straight chain" L2-siloxanes to L6-siloxanes). Concentrations of siloxane compounds in biogases can range from parts per million (ppm) levels down to parts per billion (ppb) levels. Siloxane compounds produce $SiO_2$ when burned within the turbine, promoting excessive wear and tear. Therefore, continuous monitoring of biofuel processing system for siloxanes can enable early detection and measurement of siloxane compounds. A system can use a stand-alone processor (e.g., processor 34 of FIG. 1) to quantify concentrations of siloxanes (e.g., a stand-alone FTIR that detects level of siloxane impurities in biofuels in a range of ppm levels down to ppb levels).

Figure 9:
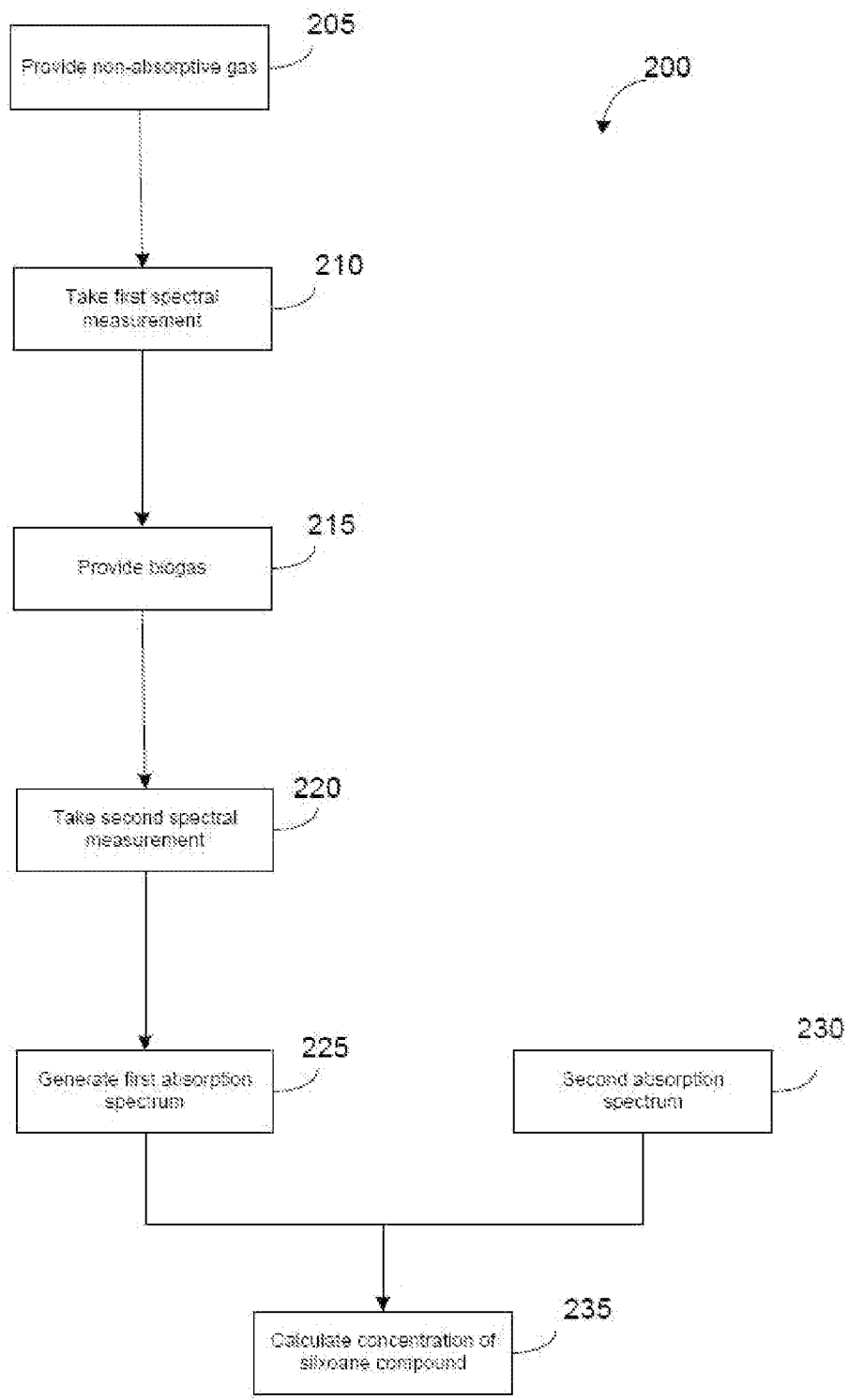
FIG. 9 shows a flowchart depicting a method for monitoring siloxane compounds in a biogas, according to an illustrative embodiment of the invention.

FIG. 9 shows a flowchart depicting an illustrative method for monitoring siloxane compounds in a biogas. The method includes the step of providing a non-absorptive gas (e.g., nitrogen or helium) to a sample cell (e.g., sample cell 33 of FIGS. 1 and 3) (Step 205). A non-absorptive gas is a gas having substantially no infrared absorptions in a specified wavelength range of interest. The method also includes the step of taking a first spectral measurement from the sample cell (e.g., a background instrumental response) (Step 210). A biogas is provided to the sample cell (Step 215). The biogas includes at least one siloxane compound (e.g., selected from a group consisting of L2-siloxane, L3-siloxane, L4-siloxane, L5-siloxane, D3-siloxane, D4-siloxane, D5-siloxane, or D6-Siloxane). The method also includes taking a second spectral measurement from the sample cell (Step 220). A first absorption spectrum is generated based on a ratio of the first spectral measurement from the non-absorptive gas to the second spectral measurement (e.g., the measurement from a sample gas comprising the biogas provided to the sample cell) (Step 225). A second absorption spectrum is generated based on, at least, a first individual absorption spectrum for a known concentration of the at least one siloxane compound in the biogas (Step 230). A concentration of the at least one siloxane compound in the biogas is calculated by using the first absorption spectrum and a second absorption spectrum (Step 235). Using, for example, CLS and/or other methods that do a direct spectral comparison, the concentration of the at least one siloxane compound can be calculated once all of the possible interferences/gases are first removed from the spectrum (e.g., the first absorption spectrum).

Both the non-absorptive gas and the biogas can be provided to a sample cell (Steps 205 and 215) so that the spectral measurements can be taken (Steps 210 and 220). The biogas can come from, for example, animal waste, wastewater or a landfill. Generally, the greater the data acquisition period (e.g., the period of time for taking spectral measurements), the lower the detection limit (e.g., lower concentrations of species can be detected). A greater data acquisition period allows for a more precise measurement (e.g., a larger signal-to-noise). If, for example, the noise is random (e.g., white noise), the signal-to-noise will increase with the square root of the acquisition period time. The second spectral measurement (e.g., Step 220) can be taken over an acquisition period of about 10 seconds to about 20 seconds. In some embodiments, the second spectral measurement from the sample cell is taken in a wavelength range of about 8 microns to about 12 microns. The step of taking the second spectral measurement can include acquiring an infrared signal from the sample cell (e.g., taking a sample of a gas comprising the biogas).

The concentration of at least one siloxane compound can be calculated (e.g., Step 235) in real time (e.g., results of quantifying concentrations of siloxane compounds obtained in seconds or minutes) and in-situ (e.g., in-line or in a device in fluid communication with a source of the biogas and without the need for grabbing a sample). Since a sample cell and processor (e.g., processor 34 of FIG. 1) can be placed in fluid communication with the source of the biogas, the analysis can be done at/substantially near the source, without the need for obtaining a sample and transporting it off site to be analyzed (e.g., as with existing GC/MS methods). The time to obtain and analyze the sample (e.g., calculate concentrations of siloxanes) can be done on the scale of seconds to minutes, dependent on the ultimate signal-to-noise needed to accurately quantify the siloxanes at the levels extant in the biogas mixture. If, for example, the signal-to-noise is not sufficient to precisely measure a particular concentration, then the acquisition time can be increased to further lower the noise (e.g., to increase the signal-to-noise). In some embodiments, a turbine generator is shut off when the concentration of at least one siloxane compound reaches a threshold value.

In some embodiments, a processor (e.g., processor 34 of FIG. 1) is used to calculate a concentration of at least one siloxane compound in the biogas (Step 235). Chemometrics, which combines spectroscopy (e.g., FTIR spectroscopy) and mathematics (e.g., multiple regression analysis), can provide clear quantitative information for siloxane compounds in the biogas. For example, the processor is used to perform multiple regression analysis using the first absorption spectrum and the second absorption spectrum to calculate the concentration of at least one siloxane compound in the biogas. Multiple regression analysis can be performed using Classical Least Squares (CLS), Partial Least Squares (PLS), Inverse Least Squares (ILS), Principal Component Analysis (PCA), and/or other chemometric algorithms.

A second absorption spectrum (e.g., from Step 230) can be generated based on, at least, the first individual absorption spectrum and individual absorption spectra for one or more additional siloxane compounds (e.g., L2-siloxane, L3-siloxane, L4-siloxane, L5-Siloxane, D3-siloxane, D4-siloxane, D5-Siloxane, or D6-siloxane), hydrocarbon compounds, water or carbon dioxide. The second absorption spectrum can be a model (e.g., a model representative of the individual absorption spectra of the agents in the biogas) based on known concentrations of the siloxane compounds, hydrocarbon compounds, water or carbon dioxide. In some embodiments, the second absorption spectrum is a model based on, at least, a first individual absorption spectrum (e.g., for a siloxane compound) and/or individual absorption spectra for one or more additional siloxane compounds, hydrocarbon compounds (e.g, methane or ethane), water or carbon dioxide.

In some embodiments, a value for the concentration for the at least one siloxane compound is determined (e.g., Step 235) such that the second absorption spectrum is substantially similar to the first absorption spectrum (e.g., mathematically fitting the model absorption spectrum to the measured absorption spectrum). By way of example, a concentration of at least one siloxane compound can be calculated by providing at least one variable representing the concentration of the at least one siloxane compound and determining a value for the at least one variable (e.g., a value for the concentration) such that that the second absorption spectrum is substantially similar to the first absorption spectrum (e.g., mathematically fitting the second absorption spectrum to the first absorption spectrum).

For example, spectral measurements can be directly linked to the actual chemical constituent using a variety of different types of quantitative analysis based upon both univariate and multivariate analysis techniques. Univariate methods include correlating spectral peak heights or areas under the spectral curve to the same characteristics for known chemical quantities of the species in the biogas. In some embodiments, this can be done using, for example, least squares regression to develop a quantitative model that predicts the actual concentrations of different species in the biogas. Another univariate method that can be used in alternate embodiments is K-Matrix or classical least squares (CLS), which is based on an explicit linear additive model (e.g., Beer's law, described in equation 1 below). CLS uses larger sections of the spectra (or the whole spectrum) in a regression with respect to all of the chemical components within the spectral region.

CLS has the limitation that it requires the concentrations of all spectrally active components be known and included in the calibration model before an adequate prediction model can be developed because, for example, unknown concentrations will reduce model accuracy. To avoid this and other complications that can arise when using univariate models, multivariate techniques are typically more useful. In one multivariate method, multiple linear regression (MLR) (also termed P-Matrix or inverse least squares (ILS)) is used to build a model using only the concentrations of the chemical components of interest (see, e.g., H. Mark, Analytical Chemistry, 58, 2814, 1986). A model may be built with this technique using only the known concentration without any unwanted effects; however, the model is limited in the number of wavelengths that can be used to describe each of the components.

Other multivariate techniques may be used in alternate embodiments that combine the ability to use large regions of the spectra to represent the constituents of interest (like that of the CLS model) with the ability of having to contend with only the constituents of interest (like that of the MLR model). In one embodiment, principal component regression (PCR) is used (as described in Fredericks et al., Applied Spectroscopy, 39:303, 1985). This method is based upon spectral decomposition using principle component analysis (PCA), followed by the regression of the known concentration values against a PCA scores matrix. Specifically, with PCR, a PCA is first made of the X-matrix resulting in a score matrix T and a loading matrix P. In the next step, a few of the first score vectors are used in a multiple linear regression with the Y-data. Where the first few components of PCA really summarize most of the information in X related to Y, PCR works nearly as well as partial least squares (PLS) for spectroscopic data, which is described below.

In another embodiment, PLS can be used to obtain actual concentration values of lesion constituents based upon spectral data (see, e.g., P Geladi and B Kowalski, Analytica Chemica Acta, 35:1, 1986, and Haaland and Thomas, Analytical Chemistry, 60:1193 and 1202, 1988). PLS is similar to PCR; however, with PLS both the spectral information and the concentration information are decomposed at the start of the method and the resultant scores matrices are swapped between the two groups. This causes the spectral information that is correlated with the concentration information to be weighted higher within the model, which can result in a more accurate model than PCR. The core of the PLS algorithm is a spectral decomposition step performed via either nonlinear iterative partial least squares (NIPALS) (see, e.g., Wold, Perspectives in Probability and Statistics, J Gani (ed.) (Academic Press, London, pp 520-540, 1975) or simple partial least squares (SIMPLS) (Jong, Chemom. Intell. Lab. Syst., 18:251, 1993) algorithms.

Further details of PCA, PCR, MLR and PLS analysis can be found in "Multi- and Megavariate Data Analysis, Part I, Basic Principles and Applications", Eriksson et al, Umetrics Academy, January 2006 and "Multi- and Megavariate Data Analysis, Part II, Advanced Applications and Method Extensions", Eriksson et al, Umetrics Academy, March 2006 the entirety of which are herein incorporated by reference.

As noted above, various chemometric algorithms (e.g., PCA, PCR, MLR, PLS) can be used to calculate concentrations of one or more siloxane compounds in a biogas. Chemometric algorithm methods are utilized to fit the overall absorption (e.g., measured spectrum based on spectral measurements from the biogas) to the absorptions of each of the constituent species (e.g., siloxanes) and provide a calculated concentration of each. Beer's law states that:

$$A_i(\tilde{v}) = a_i(\tilde{v}) b c_i \qquad \text{EQN. 1}$$

Where $A_i(\tilde{v})$ is the absorbance of species i at wavenumber $\tilde{v}$, $a_i(\tilde{v})$ is the absorptivity of the species at that wavenumber, b is the pathlength and $c_i$ is the concentration of the species. Therefore, by measuring absorbance of a species at a known concentration, it is possible to determine the absorptivity of the species for the known concentration and a given wavelength (e.g., wavenumber). An absorption spectrum can be generated by measuring the absorbance of a species, at known concentrations, for a range of wavelengths.

If there are multiple species (e.g., molecules) in a sample, Equation 1 can be modified to reflect the fact that a measured absorbance of a sample (e.g., a sample biogas in a sample cell) is the sum of the absorbances of all the species in the sample. By way of example, if a biogas includes one or more siloxane compounds, hydrocarbon compounds, water and carbon dioxide, then the measured absorbance of a biogas sample is the sum of all the absorbances of the species in the biogas (e.g., a sum of the siloxane compounds, hydrocarbon compounds, water and carbon dioxide). Accordingly, a quantitative analysis can be used to predict the actual concentrations of different siloxane compounds in the biogas.

Chemometric algorithms can be used to determine concentration of species in a sample. For example, Chemometric algorithms can be used with Equation 1 and/or other equations to determine values for concentrations such that the model spectrum (e.g., the second absorption spectrum) is substantially similar to the measured spectrum (e.g., the first absorption spectrum) (e.g., by mathematically fitting the model spectrum to the measured spectrum once all of the interfering components are removed).

Figure 10:
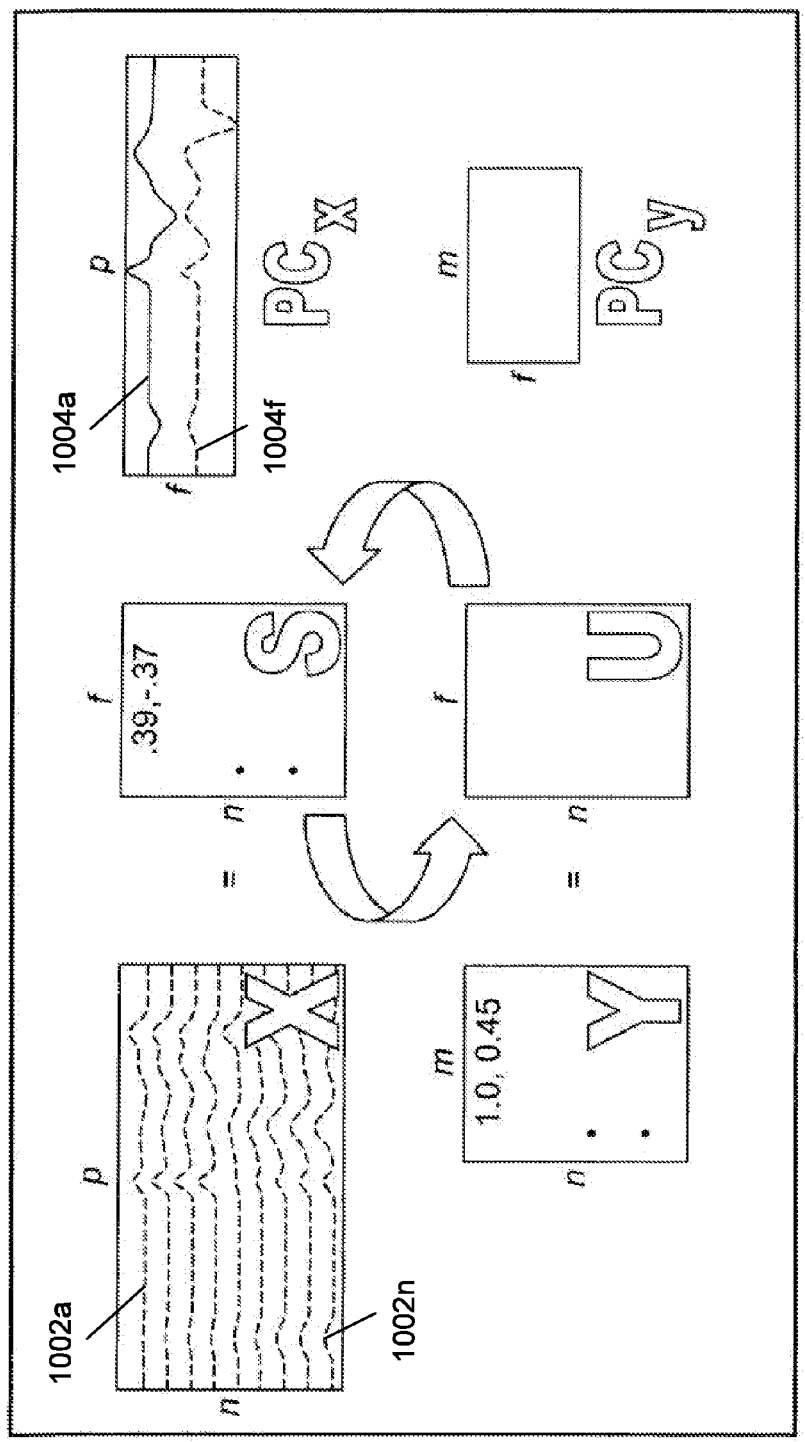
FIG. 10 shows a representation of NIPALS decomposition of spectral information represented by matrix X (spectral measurements) and matrix Y (concentration data), according to an illustrative embodiment of the invention.

In one embodiment, PLS is used to calculate the concentration of siloxane (and/or other compounds in the biogas). FIG. 10 is a diagram representing the nonlinear iterative partial least squares (NIPALS) decomposition of the spectral information represented by matrix X containing spectral measurements and matrix Y containing concentration information. PLS components of a PLS model are traditionally calculated using the NIPALS algorithm (or other similar decomposition algorithms). PLS relates two data matrices, X and Y, to each other by a linear multivariate model. In summary, a linear model specifies the relationship between a dependent or response variable y or a set of response variables Y, and a set of predictor variables X's. For example, the response variable y is concentration, and the predictor variables X are the spectral measurements 1002a through 1002n. The numbers 1.0 and 0.45 in Y are the calculated concentrations for the gas components that are in the corresponding spectrum. There are many variations on the NIPALS algorithm, which consist of a matrix-vector multiplication (e.g., X'y). S and U are resultant scores matrices from the spectral and component information, respectively. The numbers 0.39 and −0.37 in S are the scalar (score) modifiers for the basis vectors which represent the linear combination of the original set of spectra. These numbers are exemplary only of the first row of numbers that fill S and U. In this example the entire set of observed spectra are decomposed into two basis vectors, which is why there are two numbers. If the corresponding row in the PCx representation is multiplied by these numbers, the original spectrum is regenerated (e.g., minimus noise). In other embodiments, the set of observed spectra can be decomposed into any number of basis vectors. PCx and PCy are resultant principal components (or latent variables/eigenvectors) for the spectral and component information, respectively. PCx includes latent variable 1004a through 1004f. The other nomenclature in the figure is for the number of spectra (n), the number of data points per spectra (p), the number of components (m), and the number of final latent variables/eigenvectors (f).

The first decomposition for the spectral and concentration/constituent data produces a latent variable and score for each of the X and Y matrices, the scores matrix for the spectral information (S) is swapped with the scores matrix containing the concentration information (U). The latent variables from PCx and PCy are then subtracted from the X and Y matrices, respectively. These newly reduced matrices are then used to calculate the next latent variable and score for each round until enough latent variables from PCx and PCy are found to represent the data. Before each decomposition round, the new score matrices are swapped and the new latent variables from PCx and PCy are removed from the reduced X and Y matrices.

The final number of latent variables (or basis vectors) determined from the PLS decomposition (f) is highly correlated with the concentration information because of the swapped score matrices since swapping score matricies results in the spectral information being correlated with the concentration information. Advantageously, swapping leaves behind the basis vectors in both sets of matricies, which are naturally correlated to one another. The PCx and PCy matrices contain the highly correlated variation of the spectra with respect to the constituents used to build the model. The second set of matrices, S and U, contain the actual scores that represent the amount of each of the latent variable variation that is present within each spectrum. It is the S matrix values that are used in the PLS model.

In one embodiment, the PLS method is used to predict that actual compositions of the siloxane compounds in the biogas. For example the PLS algorithm can be used to predict the chemical content of the biogas directly or, for example, in the form of a percentage of compounds present (e.g., siloxane compounds, hydrocarbon compounds, water, or carbon dioxide).

In another embodiment, CLS can be used to calculate the concentration of siloxane (and/or other compounds) based on the model spectrum and the measured spectrum. In some embodiments, a sample includes two components and/or species ($s_i$ and $s_2$) in a mixture. A biogas can include more than two components/species (e.g., for example, the biogas can include different species of siloxanes, hydrocarbons, etc.), however, for the purposes of clarity, the example below assumes two components.

If a sample includes two species, then the species should vary at, at least, two wave numbers. In one embodiment, the absorbances of the two wavenumbers can be modeled using CLS based on the relationships for absorbances at each wavelength. For example, the absorbance of the first wavelength is based on a relationship of the absorptivity of the first species $s_1$ at the first wavelength, the absorbance of the second species $s_2$ at the first wavelength, the pathlength (e.g., pathlength of the sample cell 22 as described above for FIGS. 2-4), the concentration of the first species $s_1$, the concentration of the second species $s_2$, and the residual error yielded from the regression analysis of the first wavelength. Similarly, the absorbance of the second wavelength, for example, is based on a relationship of the absorptivity of the first species $s_1$ at the second wavelength, the absorbance of the second species $s_2$ at the second wavelength, the pathlength, the concentration of the first species $s_1$ and the second species $s_2$, and the residual error yielded from the regression analysis of the second wavelength.

If the pathlength is constant, then the pathlength need not be considered when determining the absorbance of each wavelength. Instead, the absorbance of the first wavelength is based on a relationship between the absorption coefficients for the first species $s_1$ at the first wavelength, the absorption coefficient of the second species $s_2$ at the first wavelength, the concentration of the first species $s_1$ and the second species $s_2$, and the residual error yielded from the regression analysis of the first wavelength. Similarly, the absorbance of the second wavelength is based on a relationship between the absorption coefficients for the first species $s_1$ at the second wavelength, the absorption coefficient of the second species $s_2$ at the second wavelength, the concentration of the first species $s_1$ and the second species $s_2$, and the residual error yielded from the regression analysis of the second wavelength.

Using the relationships described above, the absorption coefficients can be determined for a wavelength by measuring the absorbances of a sample at known concentrations. These absorbance coefficients can then be used to measure/determine unknown concentrations of species $s_1$ and $s_2$ in a sample. For example, the absorbances of the sample (e.g., the measured spectrum) can be measured at the two wavelengths, yielding values for the absorbances of the wavelength numbers, respectively. Since the absorbance coefficients are known, they can be used with the absorbance values to calculate concentrations for the species.

As noted above, a biogas can include more than two components/species. In such a case, the values for absorbances, absorption coefficients, and concentration can be modeled using the following matrices:

$$\begin{vmatrix} A_{1,1} & \cdots & \cdots & \cdots & A_{n,1} \\ \vdots & & & & \vdots \\ \vdots & & & & \vdots \\ A_{1,p} & \cdots & \cdots & \cdots & A_{n,p} \end{vmatrix} = \begin{vmatrix} K_{1,1} & \cdots & \cdots & \cdots & K_{m,1} \\ \vdots & & & & \vdots \\ \vdots & & & & \vdots \\ K_{1,p} & \cdots & \cdots & \cdots & K_{m,p} \end{vmatrix} \begin{vmatrix} C_{1,1} & \cdots & \cdots & \cdots & C_{1,n} \\ \vdots & & & & \vdots \\ \vdots & & & & \vdots \\ C_{m,1} & \cdots & \cdots & \cdots & C_{m,n} \end{vmatrix} \quad \text{EQN. 2}$$

where the "A matrix" is a matrix of spectral absorbances, the "K matrix" is a matrix representing absortivity coefficients and the "C matrix" is a matrix representing the concentrations. The number of samples (spectra) is represented by "n", the number of wavelengths used for calibrations is represented by "p" and the number of species/components is represented by "m". Equation 6 can be simplified and used to calculate the concentration of species in a sample:

$$C = A \cdot K^{-1} \quad \text{EQN. 3}$$

where $K^{-1}$ is the inverse of the K matrix. The K matrix from Equation 2 can be solved by measuring absorbances of a sample where the concentration of the individual species are known and using the following expression:

$$K = A \cdot C^{-1} \qquad \text{EQN. 4}$$

If the concentrations of individual species (e.g., siloxane compounds, hydrocarbon compounds, water, or carbon dioxide present in, for example, biogas) are known, the "C matrix" is known. The "A matrix" can be constructed based on spectral measurements obtained using, for example, the detection system of FIG. 1 (e.g., an FTIR spectrometer). Therefore, using the A matrix and the inverse of the C matrix from the known concentrations, Equation 4 is used to determine the K matrix.

Once the K matrix has been calculated from Equation 4, Equation 3 is used to calculate concentrations in a sample. An inverse of the K matrix (e.g., calculated from Equation 4 using samples with known concentrations) is used to calculate concentrations of species in a sample (e.g., siloxanes in a biogas) where the concentrations of the individual species are unknown. Spectral measurements from a sample (e.g., a sample biogas) can be obtained using a detection system (e.g., system in FIG. 1). The A matrix, representing a compilation of absorbances of the individual species in the sample, is generated based on the spectral measurements. The inverse of the K matrix and the A matrix are used in Equation 3 to calculate concentrations of the individual species in the sample.

Figure 11:
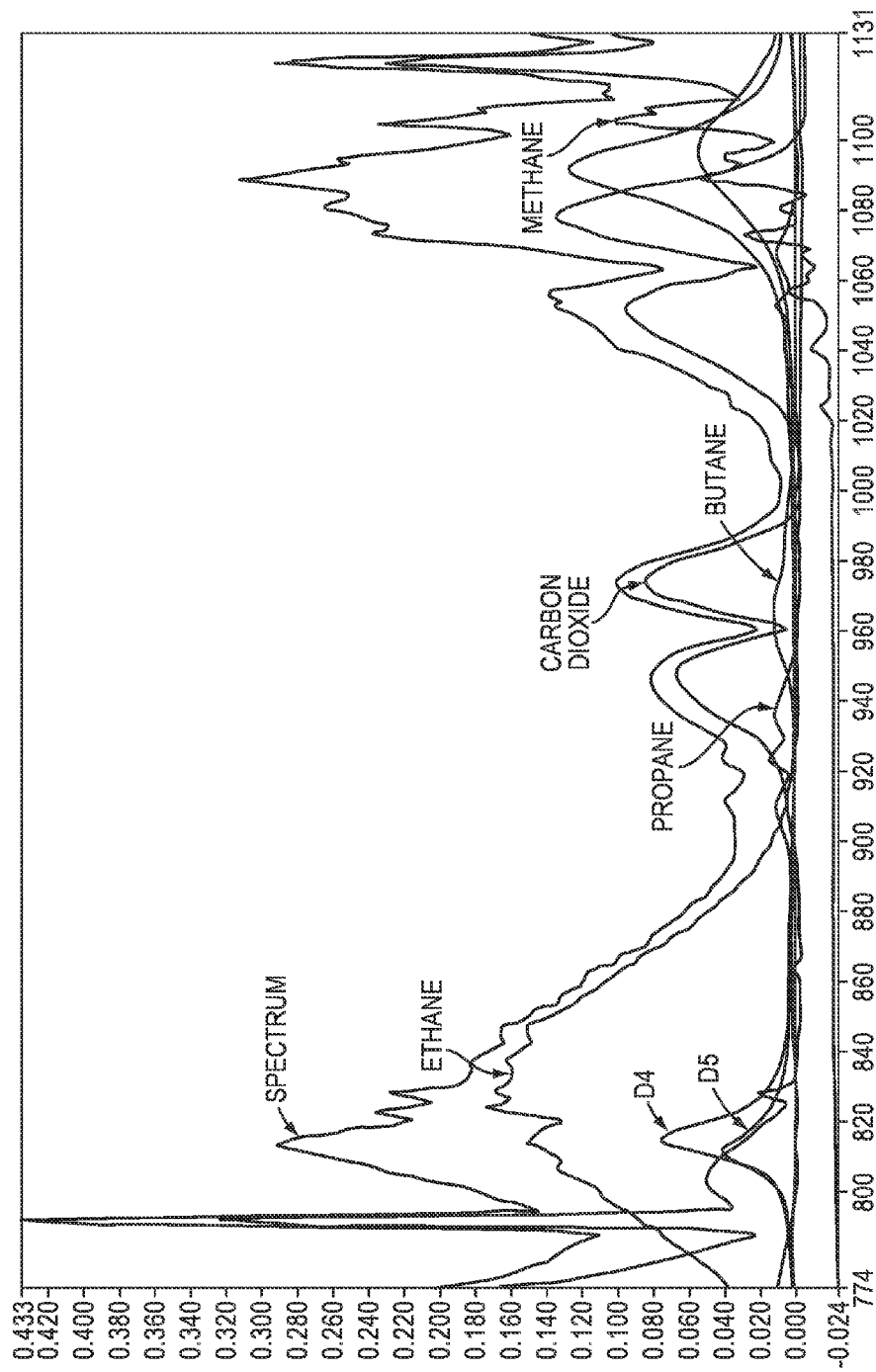
FIG. 11 shows individual absorption spectra used to monitor siloxane compounds in a biogas, according to an illustrative embodiment of the invention.

FIG. 11 shows graphical result for a CLS (i.e., classical least squares) analysis of wastewater digester gas components including 920 ppb D4-siloxane, 400 ppb D5-siloxane, 65% Methane, 35% carbon dioxide, 1400 ppm Ethane, 340 ppm Propane and 65 ppm Butane. The graph shows values for absorbances (y-axis) as a function of wavelength (i.e., wavenumber) (x-axis). Curve 300 represents the measured spectrum, curve 305 is the individual absorption spectrum for methane, curve 310 is the individual absorption spectrum for carbon dioxide, curve 315 is the individual absorption spectrum for ethane, curve 319 is the individual absorption spectrum for propane, curve 320 is the individual absorption spectrum for butane, curve 325 is the individual absorption spectrum for D4-siloxane, and curve 330 is the individual absorption spectrum for D5-siloxane. The model absorption spectrum representative of the sum of the constituent spectra 305, 310, 315, 320, 325, and 330 has not been shown for purposes of clarity because due to relatively small residual values, the model absorption spectrum would overlay the measured spectrum 300.

Data such as the spectra showed in FIG. 11 can be used to calculate concentrations of siloxane compounds (e.g., D4-siloxane and D5-siloxane). Measured/observed spectrum 300 can be used to populate values for the A matrix of Equations 7 and 10. Individual absorption spectra 305, 310, 315, 320, 325, and 330 for the individual species can be used, for known concentrations, to populate values for the K matrix and/or P matrix of Equations 7 and 10. Accordingly, the measured A matrix and the calculated K matrix and/or P matrix are used to determine values for the unknown concentrations of individual species in the measured spectrum.

In another embodiment, ILS can be used to calculate concentration of species in a sample. In CLS, absorbance is the dependent variable. In ILS, concentration becomes the dependent variable. For example, the concentration of a first species $s_1$ is based on a relationship between the linear reciprocal coefficients (which is a function of absorptivity of the first species $s_1$ at the two wavelength numbers), the absorbances at the first wavelength and the second wavelength, and the residual errors yielded from the regression analysis for the first species $s_1$. This can be simplified to the following matricies when there are several species in a sample:

$$C = P \cdot A + E_c \qquad \text{EQN. 5}$$

In Equation 5, C is a matrix of the concentrations, P is a matrix of the linear reciprocal coefficients, A is a matrix of the absorbances, and E is a matrix of the residuals. As with CLS, the P matrix can be determined using known concentrations of a sample. In this scenario, the residual error can be assumed to be zero because the ILS model can be recomputed until the residual error is sufficiently close to zero (e.g., by setting a threshold value indicative of the error being sufficiently close to zero) and Equation 5 can be modified as:

$$P = C \cdot A^{-1} \qquad \text{EQN. 6}$$

Using known concentrations for individual species yields values for the C matrix. The A matrix is constructed based on spectral measurements taken from the sample with known concentrations (e.g., using a detection system of FIG. 1, such as an FTIR spectrometer). The P matrix can therefore be calculated using Equation 6 based on spectra measured from known concentrations of species in a sample.

The P matrix can then be used with Equation 5 to solve for unknown concentrations of species in a sample. Specifically, a detection system (e.g., of FIG. 1), such as an FTIR system can be used obtain spectral measurements from a sample having unknown concentrations of individual species. The spectral measurements can be used to populate values for absorbances in the A matrix. The P matrix, calculated using Equation 6 based on known concentrations, can be used in Equation 5 to calculate a C matrix, thereby yielding the values for concentrations of individual species in the sample.

A system such as the system of FIG. 1 above can be used to detect, quantify and monitor siloxane compounds in a biogas incorporating any of the exemplary techniques as described above. The system can include, for example, a source of a first beam of radiation (e.g., source 14 of FIG. 1), an interferometer (e.g., interferometer 18 of FIG. 1), a sample cell (e.g., cell 22 of FIG. 1), a flow mechanism (e.g., flow system 82 of FIG. 3), a cooled detector (e.g., detector 30 of FIG. 1), a processor (e.g., processor 34 of FIG. 1), and a housing (e.g., housing 42 of FIG. 1) in which the source, the interferometer, the sample cell, the cooled detector and the processor are disposed. The interferometer receives a first beam of radiation from the source and forms a second beam of radiation (e.g., the second beam reflected back and forth a total of about 48 times in the sample cell, resulting in an effective pathlength of about 10.18 meters) comprising an interference signal (e.g., interferometric signal). The sample cell is in optical communication with the interferometer. The flow mechanism establishes a flow of a non-absorptive gas (e.g., a gas having substantially no infrared absorptions in a specified wavelength range of interest) and a second flow of a biogas through the sample cell (e.g., a pressured (e.g, 3-5 psig) sample (e.g., 400 mL of biogas) introduced into the sample cell, the residence time of the biogas on the order of about 5 seconds). The detector (e.g., a cooled detector) is in optical communication with the sample cell and receives a first interference signal propagating through the non-absorptive gas in the sample cell and a second interference signal propagating through a sample gas in the sample cell, the sample gas comprising the biogas. The processor is in electrical communication with the detector (e.g., a cooled detector such as a cryogenically (e.g., Stirling engine) cooled MCT (Mercury-Cadmium-Telluride) detector) and calculates a concentration of at least one siloxane compound in the biogas. The processor calculates the concentration of at least one siloxane compound in the biogas based on a first absorption spectrum and a second absorption spectrum using chemometric techniques (e.g., such as the CLS and ILS techniques). The first absorption spectrum is based on ratio of the first interference signal to the second interference signal from the detector. The second absorption spectrum is based on, at least, an individual absorption spectrum for a known concentration of the at least one siloxane compound.

In some embodiments, the sample cell (e.g., cell 22 of FIG. 1 with, for example, an optical configuration described above for FIG. 2) includes a concave reflective field surface (e.g., field surface 78 of FIG. 2) at a first end of the sample cell and a substantially spherical, concave reflective objective surface (e.g., objective surface 74 of FIG. 2) at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface.

In one embodiment, a computer readable product, tangibly embodied on an information carrier or a machine-readable storage device, is operable on a digital signal processor (e.g., processor 34 of FIG. 1) of a biogas detection system (e.g., system of FIG. 1). The computer readable product includes instructions operable to cause the digital signal processor to receive a first spectral measurement (e.g., from a detector 30 of FIG. 1) from a non-absorptive gas in a sampling cell (e.g., cell 22 of FIG. 1), where the non-absorptive gas has substantially no infrared absorptions in a specified wavelength range of interest. The computer product can also cause the digital signal processor to receive a second spectral measurement from a sample gas comprising a biogas in the sampling cell and generate a first absorption spectrum (e.g., a measured absorption spectrum) based on a ratio of the first spectral measurement and the second spectral measurement. A second absorption spectrum (e.g., a model absorption spectrum) can be generated/formulated based on, at least, a first individual absorption spectrum for a known concentration of at least one siloxane compound. The computer product can also cause the processor to calculate a concentration of one or more siloxane compounds using the chemometric techniques described above (e.g., performing a multiple regression analysis and mathematically fitting the second absorption spectrum to the first absorption spectrum to calculate a concentration of the at least one siloxane compound in the biogas).

As noted above, absorption spectra based on spectral measurements of a biogas in a sample cell and individual spectra for the individual components/species in the biogas (e.g., individual spectra of the species in a biogas, such as, for example, siloxane compounds, hydrocarbon compounds, water or carbon dioxide) can be used to calculate concentrations of individual species in a sample. Absorption spectra, such as the spectra shown in FIG. 11, can be used to generate a model based upon the calibrated absorption spectra (e.g., the second absorption spectrum as described above for FIG. 9) that are representative of a compilation of the individual absorption spectra (e.g., based on concentration ranges and/or different spectral mixtures, depending on the method(s) of analysis used). Specifically, an absorption spectrum based on spectral measurements of an unknown biogas can be used to generate an A matrix as described above, to calculate concentrations of siloxanes using, for example, Equations 7 and 11. Individual spectra, obtained based on measurements taken from known concentrations of species, can be used to generate a model spectrum representative of the individual species. Individual spectra for known concentrations can be used to calculate the P Matrix or K Matrix as described above in Equations 8 and 12. The model can include, for example, the P matrix or the K matrix (e.g., determined by using known concentrations of species) which can be used to calculate concentrations of siloxanes, using, for example, Equations 7 and 11. FIG. 11 shows spectra of data that can be used to quantify concentrations of siloxanes in a biogas, according to an illustrative embodiment of the invention. Each absorbing species in a sample has a unique absorption vs. frequency distribution (i.e. absorption spectrum). Using chemometric algorithms (e.g., multiple regression analysis), each component can be characterized and quantified, such that individual species of siloxane compounds can be detected, even in the presence of other interfering absorbers (e.g., hydrocarbon compounds such as methane or ethane).

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

While this invention has been particularly shown and described with references to preferred embodiments thereof, it will be understood by those skilled in the art that various changes in form and details may be made therein without departing from the scope of the invention encompassed by the appended claims.

What is claimed:

1. A computerized method for monitoring of siloxane compounds in a biogas, the method comprising:
   receiving, by a computing device, a first absorption spectrum that is based on a ratio of a first spectral measurement from a non-absorptive gas having substantially no infrared absorptions in a specified wavelength range of interest and a second spectral measurement from a sample gas comprising the biogas; and
   calculating, by the computing device, a concentration of at least one siloxane compound in the biogas by using the first absorption spectrum and a second absorption spectrum based on, at least, a first individual absorption spectrum for a known concentration of the at least one siloxane compound.

2. The method of claim 1, wherein calculating comprises performing, using a processor, multiple regression analysis using the first absorption spectrum and the second absorption spectrum.

3. The method of claim 2, further comprising performing, by the computing device, the multiple regression analysis using Classical Least Squares (CLS), Partial Least Squares (PLS), Inverse Least Squares (ILS) or Principal Component Analysis (PCA).

4. The method of claim 1, further comprising creating, by the computing device, the second absorption spectrum based on, at least, the first individual absorption spectrum and individual absorption spectra for one or more additional siloxane compounds, hydrocarbon compounds, water or carbon dioxide.

5. The method of claim 4, wherein the second absorption spectrum is a model based on known concentrations of the siloxane compounds, hydrocarbon compounds, water or carbon dioxide.

6. The method of claim 1, wherein the second absorption spectrum is a model based on, at least, the first individual absorption spectrum and wherein calculating comprises:
   providing at least one variable representing the concentration of the at least one siloxane compound; and
   determining a value for the at least one variable such that the second absorption spectrum is substantially similar to the first absorption spectrum.

7. The method of claim 1, further comprising calculating, by the computing device, the concentration of at least one siloxane compound in real-time and in-situ.

8. The method of claim 1, further comprising taking, by the computing device, the second spectral measurement over an acquisition period of about 10 seconds to about 20 seconds.

9. The method of claim 1, wherein the at least one siloxane compound is selected from a group consisting of L2-siloxane, L3-siloxane, L4-siloxane, L5-siloxane, D3-siloxane, D4-siloxane, D5-siloxane, or D6-Siloxane.

10. The method of claim 1, further comprising providing the non-absorptive gas and providing the biogas to a sample cell, the sample cell comprising:
    a concave reflective field surface at a first end of the sample cell; and
    a substantially spherical, concave reflective objective surface at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface.

11. A method for monitoring a level of at least one siloxane compound in a biogas, the method comprising:
    providing a non-absorptive gas to a sample cell, the non-absorptive gas having substantially no infrared absorptions in a specified wavelength range of interest;
    taking a first spectral measurement from the sample cell;
    providing a biogas to the sample cell, the biogas comprising at least one siloxane compound;
    taking a second spectral measurement from the sample cell;
    generating a first absorption spectrum based on a ratio of the first spectral measurement to the second spectral measurement; and
    calculating a concentration of the at least one siloxane compound in the biogas by using the first absorption spectrum and a second absorption spectrum, wherein the second absorption spectrum is based on, at least, an individual absorption spectrum for a known concentration of the at least one siloxane compound.

12. The method of claim 11, further comprising performing, using a processor, a multiple regression analysis to calculate the concentration of at least one siloxane compound.

13. The method of claim 11, further comprising performing the multiple regression analysis using Classical Least Squares (CLS), Partial Least Squares (PLS), Inverse Least Squares (ILS), or Principal Component Analysis (PCA).

14. The method of claim 11, wherein the second absorption spectrum is a model based on, at least, the individual absorption spectrum for the at least one siloxane compound and individual absorption spectra for one or more additional siloxane compounds, hydrocarbon compounds, water or carbon dioxide.

15. The method of claim 14, wherein the second absorption spectrum is a model based on known concentrations of the siloxane compounds, hydrocarbon compounds, water or carbon dioxide.

16. The method of claim 14, further comprising determining a value for the concentration for the at least one siloxane compound such that the second absorption spectrum is substantially similar to the first absorption spectrum.

17. The method of claim 11, further comprising calculating the concentration of the at least one siloxane compound real-time and in-situ.

18. The method of claim 11, further comprising providing the biogas from animal waste, wastewater or a landfill.

19. The method of claim 11, further comprising shutting off a turbine generator when the concentration of at least one siloxane compound reaches a threshold value.

20. The method of claim 11, further comprising taking the second spectral measurement from the sample cell in a wavelength range of about 8 microns to about 12 microns.

21. The method of claim 11, further comprising taking the second spectral measurement over a 10 second acquisition time period.

22. The method of claim 11, wherein taking the second spectral measurement comprises acquiring an infrared signal from the sample cell.

23. The method of claim 11, further comprising generating the second absorption spectrum based on, at least, an individual absorption spectra for L2-siloxane, L3-siloxane, L4-siloxane, L5-Siloxane, D3-siloxane, D4-siloxane, D5-Siloxane, D6-siloxane, Methane, Ethane, water, carbon dioxide, or an combination thereof.

24. A system for monitoring at least one siloxane compound in a biogas, the system comprising:
a source of a first beam of radiation;
an interferometer receiving the first beam of radiation from the source and forming a second beam of radiation comprising an interference signal;
a sample cell in optical communication with the interferometer;
a flow mechanism establishing a first flow of a non-absorptive gas having substantially no infrared absorptions in a specified wavelength range of interest and a second flow of a biogas through the sample cell;
a cooled detector in optical communication with the sample cell, the cooled detector receiving:
a first interference signal propagating through the non-absorptive gas in the sample cell; and
a second interference signal propagating through a sample gas in the sample cell, the sample gas comprising the biogas;
a processor in electrical communication with the cooled detector, the processor configured to calculate a concentration of at least one siloxane compound in the biogas based on:
a first absorption spectrum based on ratio of the first interference signal to the second interference signal; and
a second absorption spectrum based on, at least, an individual absorption spectrum for a known concentration of the at least one siloxane compound; and
a housing in which the source, the interferometer, the sample cell, the cooled detector and the processor are disposed.

25. The system of claim 24, wherein the sample cell comprises:
a concave reflective field surface at a first end of the sample cell; and
a substantially spherical, concave reflective objective surface at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface.

26. The system of claim 24, wherein the second absorption spectrum is a model based on, at least, the individual absorption spectrum for the at least one siloxane compound and individual absorption spectra for one or more additional siloxane compounds, hydrocarbon compounds, water or carbon dioxide.

27. The system of claim 26, wherein the second absorption spectrum is a model based on, at least, known concentrations of the siloxane compounds, hydrocarbon compounds, water or carbon dioxide.

28. A computer readable product, tangibly embodied in a non-transitory machine-readable storage device and operable to cause a data processing apparatus to:
receive, by a computing device, a first spectral measurement from a non-absorptive gas in a sampling cell, the non-absorptive gas having substantially no infrared absorptions in a specified wavelength range of interest;
receive, by the computing device, a second spectral measurement from a sample gas comprising a biogas in the sampling cell;
generate, by the computing device, a first absorption spectrum based on a ratio of the first spectral measurement and the second spectral measurement;
generate, by the computing device, a second absorption spectrum based on, at least, a first individual absorption spectrum for a known concentration of at least one siloxane compound; and
perform, by the computing device, a multiple regression analysis using the first absorption spectrum and the second absorption spectrum to calculate a concentration of the at least one siloxane compound in the biogas.

29. The product of claim 28, wherein the digital processor is configured to determine a value for the concentration of the at least one siloxane compound in the biogas such that the second absorption spectrum is substantially similar to the first absorption spectrum.

30. The product of claim 28, wherein the digital processor is configured to generate the second absorption spectrum which is a model based on, at least, the first individual absorption spectrum and an individual absorption spectra for one or more additional siloxane compounds, Hydrocarbon compounds, water or carbon dioxide.

* * * * *